US010598539B2

United States Patent
Forbes et al.

(10) Patent No.: US 10,598,539 B2
(45) Date of Patent: Mar. 24, 2020

(54) METHOD AND APPARATUS FOR INTELLIGENT AIRFLOW SENSORS

(75) Inventors: Charles E. Forbes, Millville, NJ (US); Robert E. Coifman, Millville, NJ (US)

(73) Assignee: Feather Sensors LLC, Millville, NJ (US)

( * ) Notice: Subject to any disclaimer, the term of this patent is extended or adjusted under 35 U.S.C. 154(b) by 1047 days.

(21) Appl. No.: 13/261,663

(22) PCT Filed: Nov. 23, 2011

(86) PCT No.: PCT/IB2011/055264
§ 371 (c)(1),
(2), (4) Date: May 23, 2013

(87) PCT Pub. No.: WO2012/070006
PCT Pub. Date: May 31, 2012

(65) Prior Publication Data
US 2013/0245980 A1  Sep. 19, 2013

Related U.S. Application Data

(60) Provisional application No. 61/458,460, filed on Nov. 23, 2010.

(30) Foreign Application Priority Data

Dec. 3, 2010  (WO) .................. PCT/IB2010/055559

(51) Int. Cl.
*G01F 25/00*  (2006.01)
(52) U.S. Cl.
CPC ............................. *G01F 25/0007* (2013.01)

(58) Field of Classification Search
CPC combination set(s) only.
See application file for complete search history.

(56) References Cited

U.S. PATENT DOCUMENTS 4,227,507 A * 10/1980 Takase et al. .................. 123/492
4,712,529 A * 12/1987 Terasaka et al. ............. 123/492
(Continued)

FOREIGN PATENT DOCUMENTS

WO  WO 97/05824  *  2/1997  ............. A61B 5/087
WO  WO 02/41777  *  5/2002  ............. A61B 5/087

OTHER PUBLICATIONS

Written Opinion of the International Searching Authority dated May 28, 2013.*

*Primary Examiner* — Huan H Tran
(74) *Attorney, Agent, or Firm* — Brian K. Johnson, Esq., LLC

(57) ABSTRACT

A sensor capable of detecting both airflow in spirometry and a full range of sound frequencies is provided. The airflow sensor includes a movable flap with one or more integrated strain gauges for measuring displacement and vibration. The sensor may be a bidirectional elastic flap airflow sensor that is capable of providing data needed for both spirometry and auscultation measurements. The sensor is provided in connection with a software module that analyzes sensor output waveforms and provides for correction functions that correct for certain non-linear response functions of the flap. The correction functions are also suitable for non-medical fluid flow metering applications. Additional devices may also be affixed to the flap, such as sensors for the ambient level of various chemicals, sensors for temperature, sensors for humidity and microphones.

13 Claims, 31 Drawing Sheets

(56) References Cited

U.S. PATENT DOCUMENTS

2004/0254492 A1* 12/2004 Zhang et al. ............... 600/538
2011/0092840 A1*  4/2011 Forbes et al. ............... 600/538
2012/0277615 A1* 11/2012 Coifman et al. ............ 600/538

* cited by examiner

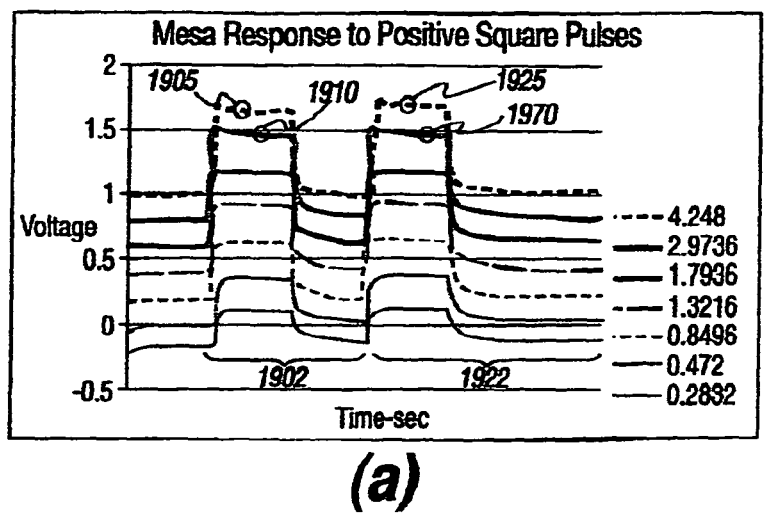
*(a)*
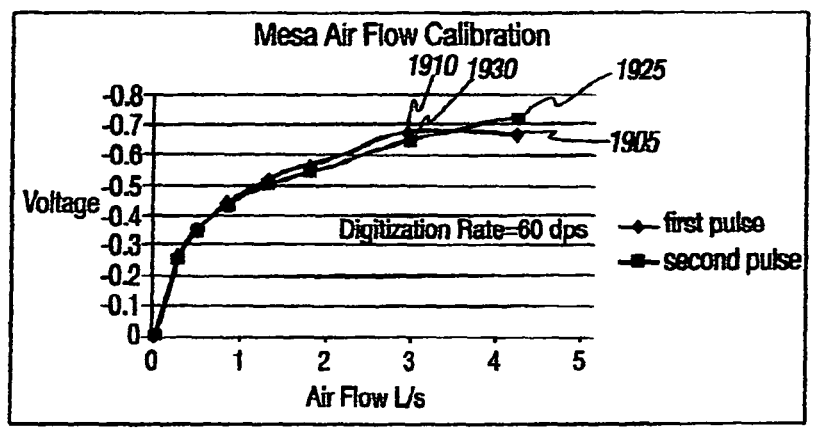
*(b)*
Fig. 18

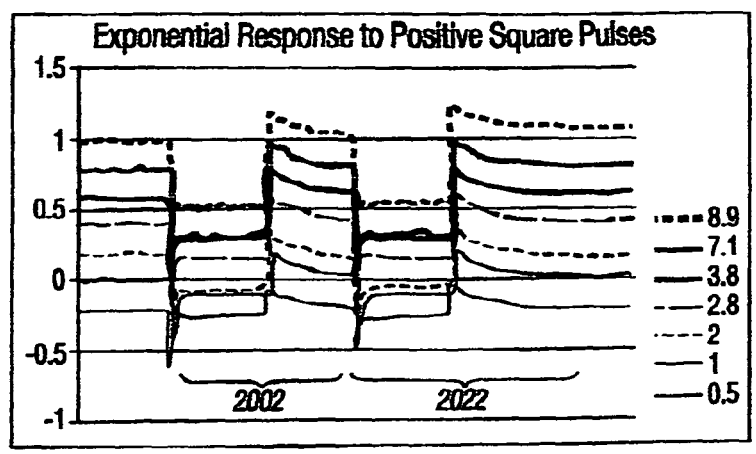
*(a)*
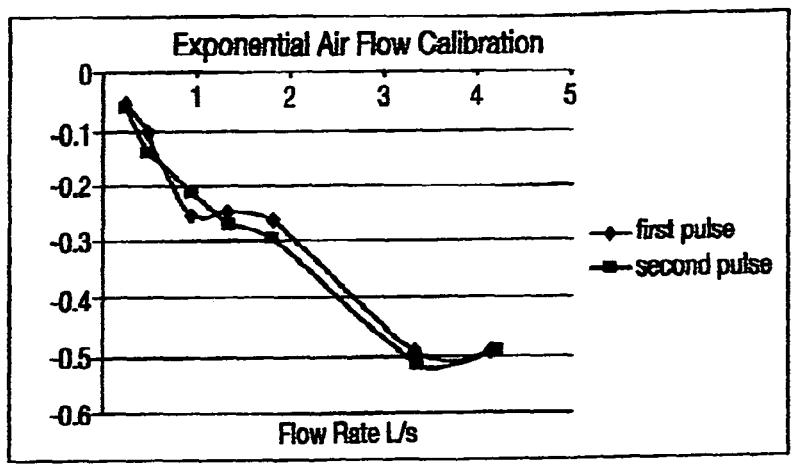
*(b)*
Fig. 19

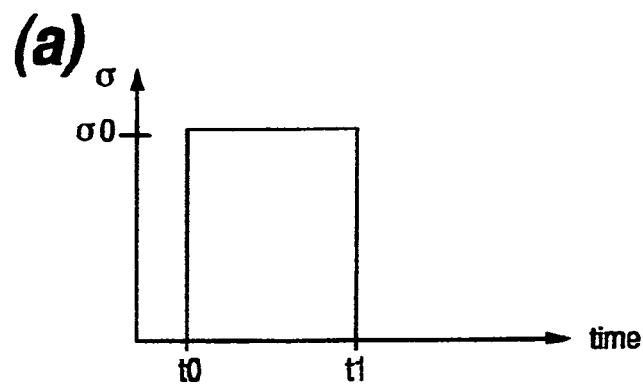
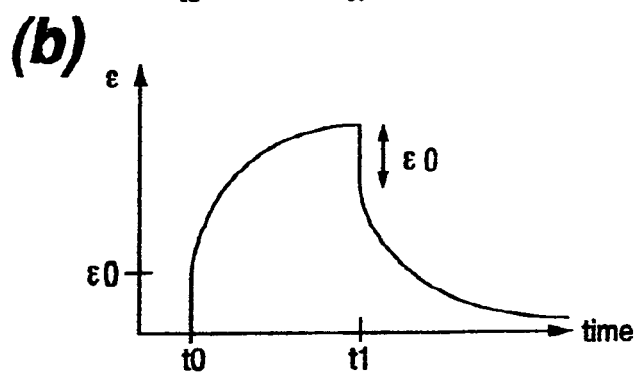
(c) $\sigma(t) = E\varepsilon(t) + n \dfrac{d\varepsilon(t)}{dt}$
(d) $\varepsilon(t) = \sigma C_0 + \sigma C \displaystyle\int_0^\infty f(\tau)\,(1 - \exp[-t/\tau])\,d\tau$
Fig. 21

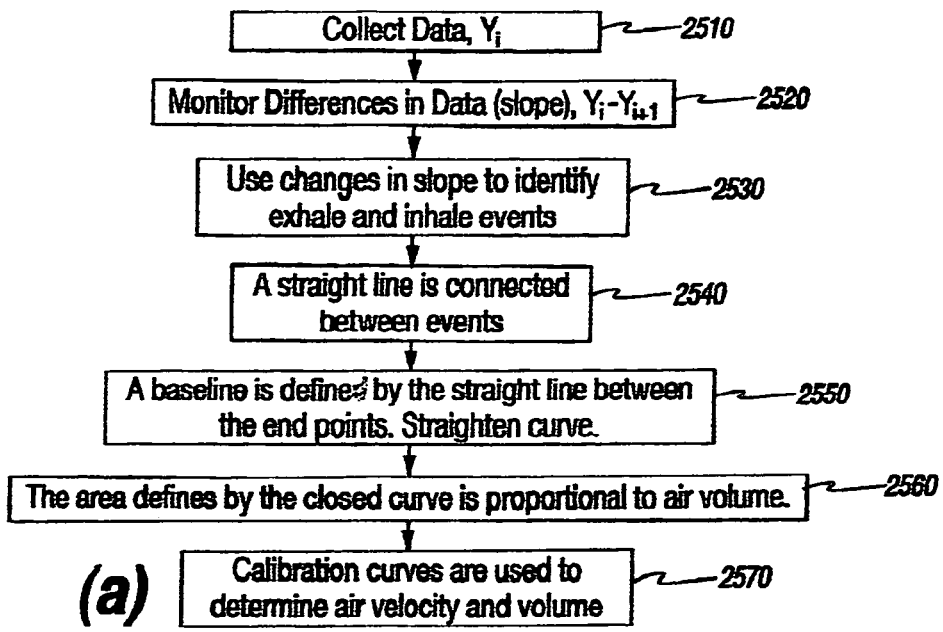
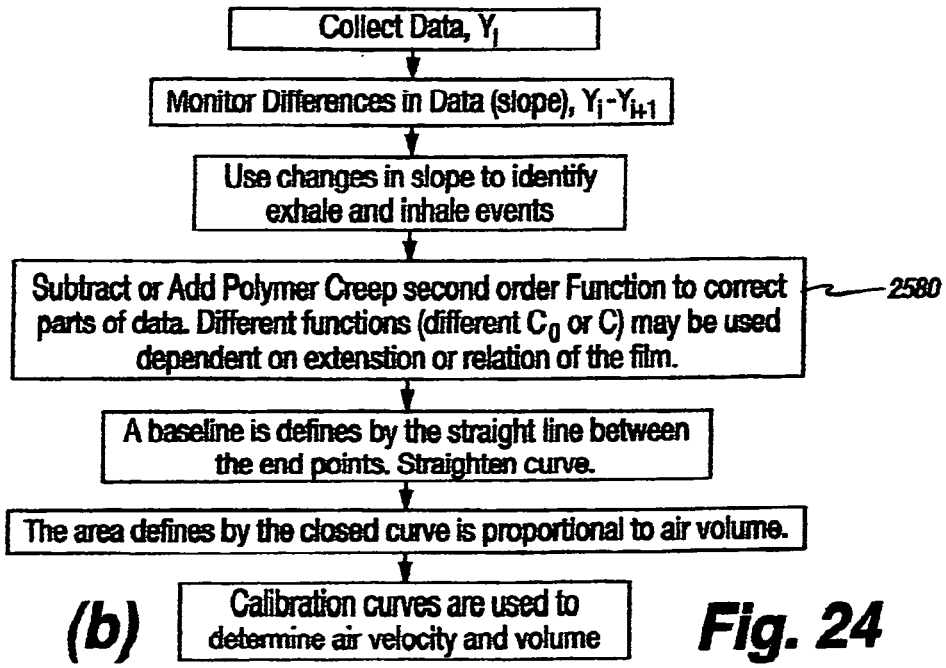
Fig. 24

METHOD AND APPARATUS FOR INTELLIGENT AIRFLOW SENSORS

RELATED APPLICATIONS

This application claims priority to the U.S. Provisional Patent Application Ser. No. 61/458,460, titled "Apparatus for Intelligent Airflow Sensors," filed on Nov. 23, 2010 the contents of which is herein incorporated by reference in its entirety.

This application also claims priority to the U.S. patent application Ser. No. 12/885,391 titled "Intelligent Air Flow Sensors," filed on Sep. 17, 2010 and the PCT Patent Application No. PCT/IB2010/055559 titled "Method and Apparatus for Intelligent Flow Sensors," filed on Dec. 3, 2010 the contents of all of which are also herein incorporated by reference in their entirety.

FIELD OF THE INVENTION

The disclosure relates generally to airflow sensors for use in spirometry, forced oscillation techniques, impulse oscillometry and the analysis of sounds from the respiratory tract. More specifically, the disclosure relates to the determination of a correction function that is applied to the output sensor data from the measured airflow to accommodate for non-linear characteristics in the flap response function.

BACKGROUND OF THE INVENTION

Chronic obstructive pulmonary disease (COPD) affects between 15 million and 30 million Americans and is the fourth leading cause of death in the United States. COPD generally describes long-standing airway obstruction caused by emphysema or chronic bronchitis. COPD includes the class of diseases characterized by relatively irreversible limitations of airflow in the lungs. The most familiar common disease in this class of diseases is emphysema, in which the air sacs of the lung become damaged and/or destroyed, and unable to participate in air exchange. Another common respiratory disease is asthma, which is characterized by wheezing, coughing, chest tightness, and shortness of breath. Wheezing is a mid-frequency pitched, whistling or sibilant sound caused by airway narrowing due to inflammation in the airways and/or secretions in the airways. The muscles surrounding the airways become tight and the lining of the air passages swell. This reduces the amount of air that can pass by, which leads to wheezing sounds. Spirometry is a well known standard for the diagnosis and management of COPD.

Spirometry is a physiological test that measures how an individual inhales or exhales volumes of air as a function of time. The primary signal measured in spirometry may represent volume or flow. The spirometry is typically performed using a spirometer. The spirometer may provide graphs, called spirograms, as a result of the measurements. The spirograms may illustrate a volume-time curve and/or a flow-volume loop. An exemplary flow-volume loop 100 is illustrated in FIG. 1.

The most common parameters measured in spirometry are illustrated in FIG. 1. These parameters are Forced Vital Capacity (FVC), Forced Expiratory Volume at timed intervals of 0.5, 1.0, 2.0, and 3.0 seconds ($FEV_{1/2-3}$), Forced Expiratory Flow 25-75% ($FEF_{25-45}\%$), Forced Inspiratory Flow 25-75% ($FIF_{25-75}\%$) and Peak Expiratory Flow Rate (PEFR). FVC is the volume of air that can forcibly be blown out after full inhalation, measured in liters. $FEF_{25-75}\%$ is the average rate of expiratory airflow from the 25% volume point to the 75% volume point of the expiratory effort, usually expressed in liters per second. $FEF_A\%$ is the momentary expiratory flow rate at "A" % of maximal expiratory effort, usually expressed in liters per second. FIF is similar to FEF except the measurement is taken during inhalation. PEFR is the maximal flow (or speed) achieved during the maximally forced exhalation initiated at full inhalation, measured in liters per minute. PEFR can be measured with spirometers or with simpler mechanical or electronic peak flow meters, discussed below.

Elastic flap airflow sensors have been used in human respiratory medicine for unidirectional measurement, i.e. measurement during inhalation or exhalation, of airflow in mechanical peak flow meters. An elastic flap airflow sensor may be defined as an airflow sensor with a flow-sensing member. The flow-sensing member may be a flap positioned so that it is moved by the airflow to be measured without creating enough resistance to significantly impede the airflow to be measured. The pressure of oncoming air against the flap causes elastic displacement, typically by bending. Airflow is measured by measuring the elastic displacement or deformation of the flap.

In mechanical elastic flap peak flow meters, the flap is typically made of a flat steel spring which provides low resistance to the airflow. The flap pushes a low resistance pointer along a track as the flap is displaced due to the airflow. The pointer remains at the position of maximum displacement while the flap falls back as the rate of airflow decreases. The flap returns to its "zero flow" position at the end of the expiratory effort. PEFR may be read directly from the position of the pointer at the end of the breath, after which the pointer is manually returned to the "zero" position for the next effort.

In U.S. Pat. No. 6,447,459, Larom discusses measuring human expiratory airflow using a steel spring elastic flap flow-sensing plate. In Larom, the displacement of the steel spring elastic flap is tracked using a strain gauge or other sensor types. Larom discusses mechanisms to damp the vibrations of the flap both before and after the achievement of maximum displacement. However, the solutions proposed by Larom either make the device non-portable, i.e. in the case of electromagnetic damping, or create surface irregularities, i.e. the use of lever and vanes, which can trap mucus and other respiratory secretions. As a result, Larom's device becomes difficult to clean and disinfect to meet regulatory requirements for other than single patient use. Another issue with Larom's device is that the sensor can only provide unidirectional airflow measurement, i.e. either during inhalation or exhalation. Larom's device further fails to measure sonic vibration of the pulmonary function such as lung sounds indicating abnormal lung function, i.e. wheezing. Specifically, the damping needed for Larom's sensor to accurately record the deflection of the steel spring elastic flap also damps and hence eliminates the sonic vibration.

A pneumotachometer is another conventional type of device that can be used for measuring the flow of respiratory gases. A pneumotachometer is a device to measure respiratory airflow by measuring the pressure drop across a fixed resistance. FIGS. 2A and 2B illustrate conventional pneumotachometers. Specifically, FIG. 2A illustrates an exemplary Fleisch-type pneumotachometer 202 and FIG. 2B illustrates an exemplary Lilly-type pneumotachometer 208. In the Fleisch-type pneumotachometer 202, the fixed resistance is an array of capillaries while in the Lilly-type pneumotachometer 208, the fixed resistance is a partially obstructing mesh or membrane.

In the Fleisch-type pneumotachometer 202 illustrated in FIG. 2A, the flow (V') is measured in a tube with a small, fixed resistance. The resistance to flow comes from an array of capillaries 206 arranged in parallel to the direction of flow. Accurate measurements with the Fleisch-type pneumotachometer 202 are best performed when the flow pattern is laminar and the flow is linearly related to pressure drop.

In the Lilly-type pneumotachometer 208 illustrated in FIG. 2B, the flow (V') is derived from the pressure difference over a small, fixed resistance, produced by a fine metal mesh 210. Accurate measurements with the Lilly-type pneumotachometer 210 are best performed when the flow pattern is laminar and the flow is linearly related to pressure drop.

However, as indicated above, the pneumotachometers only measure the flow of respiratory gases. Thus, pneumotachometers fail to measure the sonic properties of the forced vital capacity maneuver. Moreover, the sampling rate associated with the conventional Fleisch-type and Lilly-type pneumotachometers is the standard sampling frequency of 50 Hz. This sampling rate is insufficient for measuring the sonic vibration associated with respiration, which may have components with frequencies as high as 1000 Hz or higher.

Other methods for measuring the respiratory function are the conventional Forced Oscillation Technique (FOT) and the conventional Impulse Oscillometry (IOS). FOT and IOS are techniques to measure the impedance of the airway by superimposing pressure fluctuations of known frequency and intensity on tidal breathing and analyzing the resulting perturbations of pressure and airflow. The two techniques differ in that in FOT, the superimposed pressure fluctuations are continuous and continue during measurement of the resulting flow and pressure perturbations. On the other hand, in IOS, the superimposed pressure fluctuations consist of short pulses, where the resulting perturbations are measured between pulses. The principal advantage of FOT and IOS compared to spirometry is that FOT and IOS do not depend on the performance of forced respiratory maneuvers by the patient or the source of airflow under analysis. Thus, it is possible to measure airway impedance with FOT and IOS in infants and children too young to cooperate in spirometry, in patients who are unconscious, and in non-human vertebrate animals. Disadvantages of FOT and IOS include the high cost, complexity and delicacy of presently available equipment and the consequent paucity of normative data for measurements in health and disease.

FIG. 2C illustrates an exemplary device 212 for IOS. The device 212 includes an impulse generator 214 and a pneumotachometer 216 attached to a mouthpiece 218. A metal screen 250 is provided in the pneumotachometer 216. A terminal resistor 220 and the impulse generator 214 are connected to the pneumotachometer 216 via a Y-adapter 222. A flow transducer 224 and a pressure transducer 226 are connected to the pneumotachometer 216 for measuring the flow and the pressure of the respiratory gases, respectively. The measurements of the flow transducer 224 and the pressure transducer 226 are conveyed to a digital signal processor 228. The output of the digital signal processor 228 is provided to a loudspeaker 230 and a computer 232.

The device 206 illustrated in FIG. 2C can be used in performing IOS by measuring various parameters of airway impedance as a function of pressure pulse frequency across a range from 5 to 40 Hz. The resulting signals are electronically separable from the airflow changes of spontaneous respiration, which occurs at frequencies from about 0.1 Hz to 5 Hz. As indicated above, the sonic vibration associated with respiration may have components with frequencies as high as 1000 Hz.

The device 206 illustrated in FIG. 2C may also be used for FOT if speaker output is continuous rather than pulsed. Energy may be applied at one frequency, at several frequencies in sequence, or at multiple frequencies simultaneously using pseudo-random noise. The ratio between the pressure drop across the airway and the airflow at a frequency included in the speaker output is defined as the impedance of the airway, by analogy to electrical impedance. The respiratory impedance is a complex quantity, e.g. including a real part and an imaginary part or an amplitude component and a phase component. The respiratory impedance may be used to determine the oscillatory pressure component in phase with flow and oscillatory flow amplitude.

SUMMARY OF THE INVENTION

The present invention provides for a fluid flow sensing system having a housing with a chamber that is sized and dimensioned to allow fluid to pass therethrough, a flap provided within the chamber, wherein the fluid causes the flap to move when the fluid passes thereover, a sensor coupled to the flap for generating an output signal when the flap moves, the sensor configured to sense a displacement of the movable flap in at least two directions; a determining unit for receiving the output signal of the sensor and in response thereto, determining flow rate data associated with the fluid; and a correction unit for receiving the flow rate data and applying a correction function to the flow rate data to correct for a non-linear response of the flap.

According to other aspects of the invention, the non-linear response is an exponential decay of the flap response and the correction function corrects the exponential decay, or alternatively the correction function is a straight line approximation, or alternatively the correction function is an exponential function based upon the exponential decay. In other aspects, the non-linear response is a baseline drift of the flap response and the correction function corrects for the baseline drift. In still other aspects of the invention, the baseline drift is integrated over time to create the correction function, and the correction function is empirically determined. Additionally, the sensor may be a piezoresistive sensor and the determining unit may include a voltage conversion unit for receiving the output signal of the sensor and converting the output signal into a voltage output signal; an amplification unit for receiving the voltage output signal and generating an amplified voltage output signal; a converter for converting the amplified voltage output signal into a digital output signal; and a calculation unit for determining the air flow rate of the air based upon the digital output signal. In this aspect, the determining and correction units are provided as software modules within a general purpose computer, the general purpose computer coupled to the sensor and including a processor and a memory.

A method provided according to one aspect of the present invention uses a sensor coupled to a flap, said sensor generating an output signal when said flap moves, and includes the steps of providing a flow of said fluid across said sensor; sensing a displacement of said flap with said sensor, said displacement being representative of a flow rate associated with said fluid flow; generating said output signal from said sensor; determining from said output signal said flow rate of said fluid flow from said sensed displacements; and correcting said flow rate data by applying a correction function to correct a non-linear response of said flap.

According to other aspects of the method, said non-linear response is an exponential decay of said flap response and said correcting step includes approximating said correction with a straight line; said non-linear response is an exponential decay of said flap response and said correcting step includes applying an exponential decay correction function; said non-linear response is a baseline drift of said flap response and said correcting step includes applying a baseline drift correction function; or said step of applying said baseline drift correction function includes integrating portions of said flow rate data. In still other aspects of the method, said step of determining further includes converting said output signal into a voltage output signal; generating an amplified voltage output signal from said voltage output signal; and determining said flow rate based on said amplified voltage output signal. In a final aspect of the invention a computer-readable media is provided having executable instructions for causing a processor within a computer-based system to perform the above-mentioned method steps.

BRIEF DESCRIPTION OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein:

FIGS. 18($a$) and 18($b$) show a series of sensor response functions and a resulting calibration curve respectively according to one aspect of the present invention;

FIGS. 19($a$) and 19($b$) show another series of sensor response functions and a resulting calibration curve respectively according to one aspect of the present invention;

FIGS. 21($a$) through 21($g$) provide a stress-strain profile illustrating polymer creep along with accompanying mathematical relationships governing the same;

FIGS. 24($a$) and ($b$) provide method flow diagrams for first and second order sensor response corrections according to one aspect of the present invention;

DETAILED DESCRIPTION OF THE INVENTION

The present invention provides an airflow sensor that is capable of measuring bidirectional airflow of a patient, as well as clinically relevant breath sounds associated therewith. Breath sounds include sounds that are associated with inhalation and exhalation of humans and/or animals. Specifically, the airflow sensor used according to the teachings of the present invention is capable of simultaneously detecting auscultation data and airflow data. The airflow sensor generates an output signal in response to the presence of airflow. The generated output signal is representative of both the airflow data including airflow rate, and the breath sound data associated therewith.

According to various embodiments of the present invention, a single sensor is provided for sensing both the airflow in spirometry and the full range of sound frequencies needed to track clinically relevant breath sounds in auscultation. Any suitable type of sensor can be used provided it is capable of sensing both airflow and breath sounds while simultaneously providing an appropriate output signal that is representative of or can be correlated to the patient's airflow and breath sounds. Examples of sensors suitable for this purpose include strain gauges and piezoresistive or piezoelectric sensors. According to a preferred embodiment, the present invention employs a thin film sensor mounted in an airflow chamber. The thin film sensor may be a piezoresistive sensor that is sensitive to bending. An amplified signal output from the sensor consists of a direct current (DC) electrical component that measures airflow (spirometry) and a high frequency alternating current (AC) audio component that is representative of sound from the lungs (auscultation) during the inhalation and exhalation cycles of respiration.

Particular implementations of the present invention may provide one or more of the advantages provided herein. The airflow sensor described in the present application not only overcomes the above-listed limitations of conventional spirometers but also provides the simultaneous, direct sensing or detection of sound from the airway. The piezoresistive airflow sensor of the present invention may also be used in connection with the conventional FOT or IOS instrumentation to replace the pneumotachometer airflow sensors. Thus, it is possible to produce FOT or IOS instruments at lower cost. Replacing the pneumotachometer of the conventional FOT or IOS instrumentation with the piezoresistive airflow sensor of the present invention results in a more stable, portable, easier to use and easier to maintain FOT or IOS device. The simpler design and greater stability in the FOT or IOS device afforded by the present invention allows the FOT or IOS device to enter the mainstream of clinical medicine.

Figure 3:
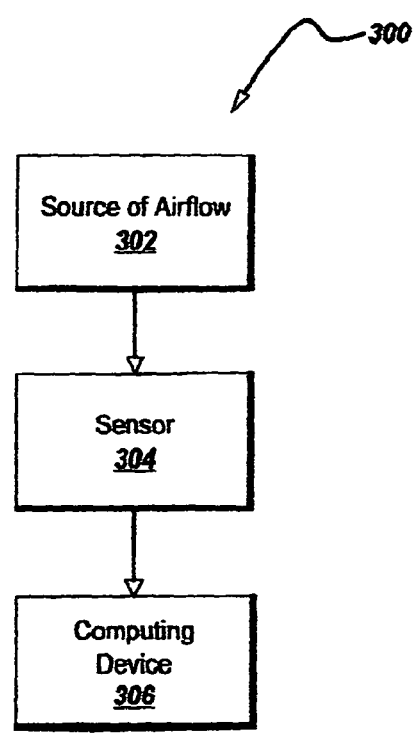
FIG. 3 is a general block diagram view of a system for measuring airflow and breath sounds according to the techniques of the present invention.

FIG. 3 is a schematic block diagram of a system 300 for generally measuring, collecting, analyzing, processing and/or gathering airflow and sound data. If configured for task-appropriate data analysis, the system 300 may be used for any of spirometry, FOT or IOS. The system 300 includes the sensor 304 of the present invention. The sensor 304 is connected to a source of airflow 302 to be analyzed. The airflow can be provided, for example, by a patient. The sensor 304 may be provided in a mouthpiece that allows measuring characteristics of the air flowing in and out of the lungs of the source of airflow 302. The readings of the sensor 304 may be sent to a computing device or system 306 for further analysis. The computing device 306 may include one or more processors, one or more storage devices, or one or more filters or other associated processing circuitry, and a display device. The various components of the computing device 306 can be located in a single location or can be distributed throughout the system 300. The illustrated computing device processes the output signal generated by the sensor 304 and is capable of determining the airflow rate and breath sounds associated with the source 302.

Figure 4A:
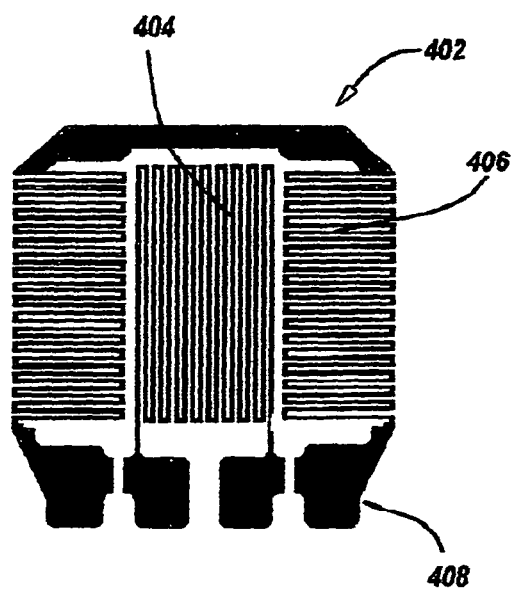
FIG. 4A is a schematic depiction of an exemplary airflow sensor according to an exemplary embodiment of the present invention.

FIG. 4A is a general schematic depiction of an exemplary sensor 304 according to one embodiment of the present invention. Specifically, FIG. 4A illustrates a piezoresistive sensor 402 that has two orthogonal piezoresistive circuits 404, 406 for measuring both sound and spirometry data. The resistance of both circuits may be about 120 ohms. The inner circuit 404 may be sensitive to spirometry data while the outer circuit 406 may be sensitive to high frequency sounds. The sensor 304 of the present invention may be sensitive to sounds with frequencies between about 1 Hz and about 1000 Hz. Preferably, the sensor 304 of the present invention is sensitive to sounds with frequencies between about 35 Hz and about 1000 Hz. A plurality of pads 408 are provided at a lower end of the sensor 402 for connecting the sensor 402 to other system circuitry.

The piezoresistive sensor 402 illustrated in FIG. 4A is provided for illustrative purposes only and should not be construed in a limiting sense. The sensor 304 of the present invention may also employ a single piezoresistive circuit that is sensitive to both spirometry data and high frequency sounds.

The sensor 402 used in the present invention may consist of a grid of metallic wire bonded to polyimide or polymer films such as polyethylene terephthalate (PET), nylon, polypropylene or polyethylene. The metallic wire may be made of constantan, i.e. a copper-nickel alloy consisting of about 55% copper and 45% nickel. Constantan has a resistivity that is constant over a wide range of temperatures. Alternatively, the metallic wire may be made of gold, chromium, aluminum, etc. Aluminum or steel has much less flexibility than constantan.

The piezoresistive sensor 402 may be constructed by deposition techniques, for example, vacuum deposition, electroplating, and printing procedures familiar in the semiconducting fabrication field. FIG. 4A illustrates an exemplary pattern of constantan deposited on polyimide for measuring strain in two perpendicular directions. As provided above, the sensor 402 of the present invention may be formed by depositing constantan in polyimide in a single direction. The metallic wire may be deposited on polyimide using E-beam or sputtering deposition techniques. Photolithography mask, shadow masks, and electrophotographic imaging may be used in conjunction with E-beam deposition techniques in manufacturing the strain gauge. Optionally, various coatings may be applied to the strain gauge for protecting the circuit from oxidation or water aging.

Conventionally, a polyimide-backed strain gauge is used to measure the strain of a carrier medium such as a piece of aluminum, or steel, to which the polyimide flap is glued. When the carrier medium is strained, the length of the grid changes, which causes a change in the electrical resistance. A Wheatstone bridge may used to monitor the change in resistance and produce an output voltage proportional to the strain in the carrier medium.

Contrary to the conventional strain gauges where the gauge is glued directly onto the carrier medium, in producing the airflow sensor of the present invention, the sensor is attached to the carrier medium at one end. Thus, the sensor becomes integrated with a bendable flap. In the present invention, the polyimide flap itself is the target of the measurement.

Figure 4B:
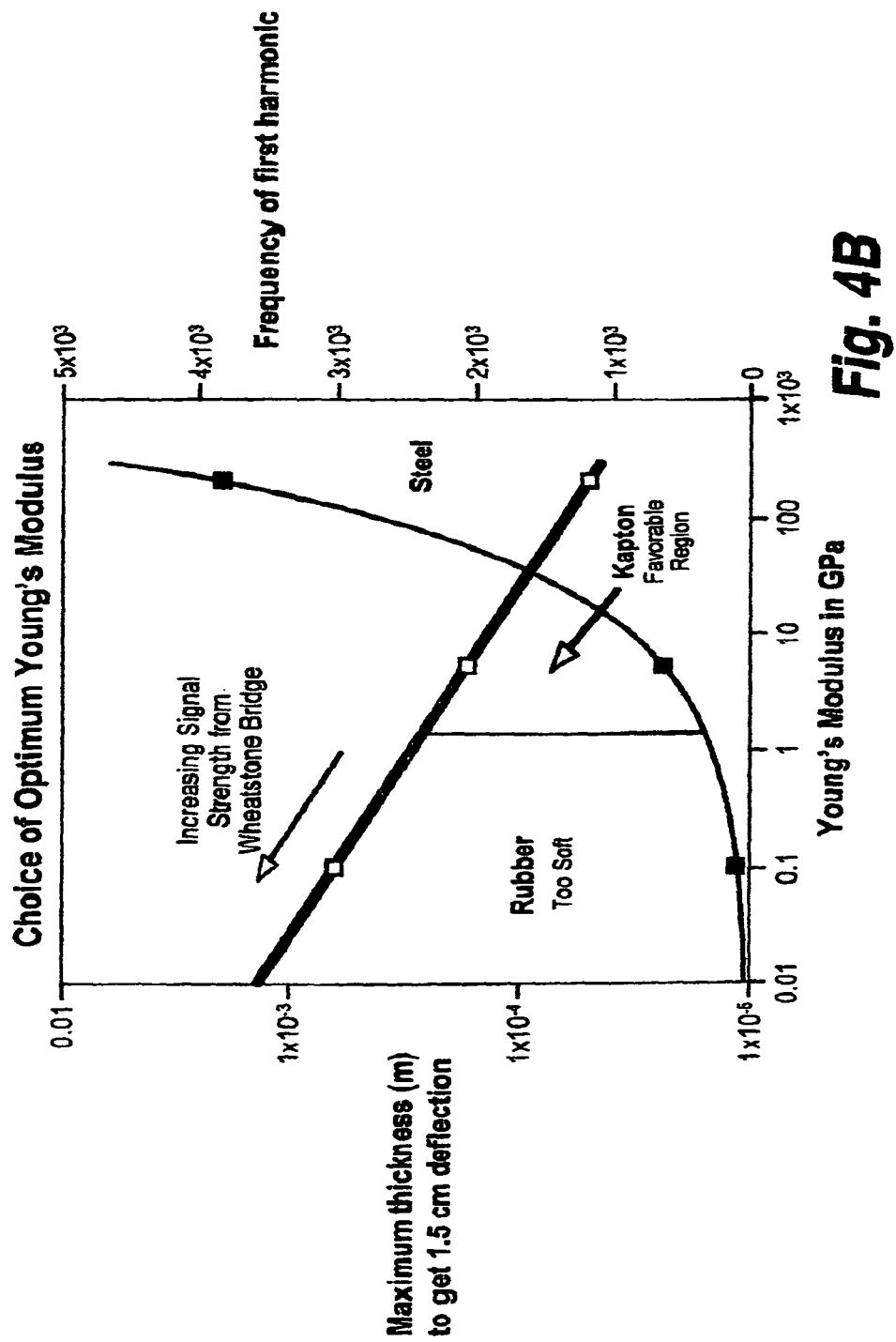
FIG. 4B is a graphical depiction of an exemplary mode analysis examining the effect of Young's modulus on the frequency of a first vibrational mode of an exemplary sensor and according to the teachings of the present invention.

According to various embodiments of the present invention, Kapton® may be used as the carrier medium for the sensor. Kapton® is a polyimide film that remains stable in a wide range of temperatures, i.e. from −269 to +400° C. (−452 to 752° F.). FIG. 4B illustrates a mode analysis examining the effect of Young's modulus on the frequency of the first vibration mode of the sensor using a one dimensional model. FIG. 4B further illustrates the thickness of a backing required to obtain a 1.5 cm deflection. For a given pressure, stiff materials, such as steel, need to be very thin. For such materials the frequency of the first vibration mode is high. Softer materials, such as rubber, have a lower frequency but are generally thicker. Thicker materials are desirable since a larger signal is observed from the sensor. The present inventors have realized that a reasonable compromise between the two extremes is found where the two curves intersect on FIG. 4B. The intersection point illustrates the properties of Kapton®.

Kapton® is a polymer that has a glass transition temperature of greater than 350° C., a coefficient of thermal expansion of $12 \times 10^{-6}/°$ C., and a RMS surface roughness of approximately 30 nm for the film Kapton® polyimide films have low shrinkage properties, i.e. a 75 µm thick foil shrinks approximately 0.04% after about 2 hours at about 200° C. The film has a relatively low humidity expansion coefficient of $9 \times 10^{-6}/\%$ RH, a water permeability of 4 g/m2/day, oxygen permeability of 4 cm3/m2/day, and water absorption of 2.4%. The bulk modulus of Kapton® E is 780 Kpsi. However, the use of Kapton® in accordance with the present invention is for illustrative purposes only and should not be construed in a limiting sense.

Figure 4C:
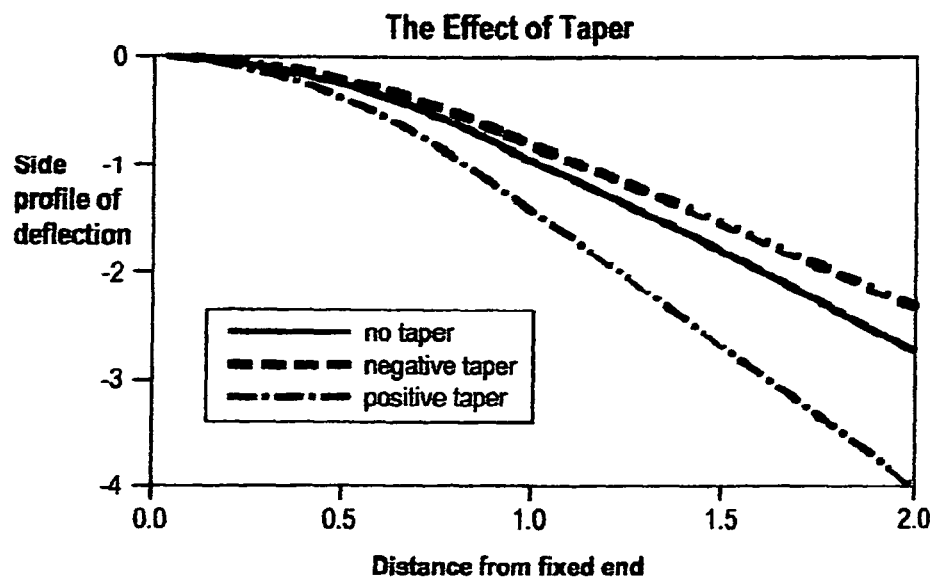
FIG. 4C is a graphical depiction of the effects of a tapered design during bending of an exemplary flap used in the system of FIG. 3 according to the teachings of the present invention.

According to various embodiments of the present invention, the flap 450 may be a tapered surface. FIG. 4C graphically depicts the performance of the flap with and without a taper. Specifically, the graphical lines illustrate how the side profiles of the flaps bend under pressure. A positive taper can be used in connection with the present invention. A flap with a positive taper has a fixed end that is thicker than the free end. A flap with a negative taper has a free end that is thicker than the fixed end. During bending, the maximum curvature that is proportional to change in resistance occurs at the fixed end. As illustrated in FIG. 4C, larger signals are generated using a flap with a positive taper rather than using a flap with no taper.

Figure 4D:
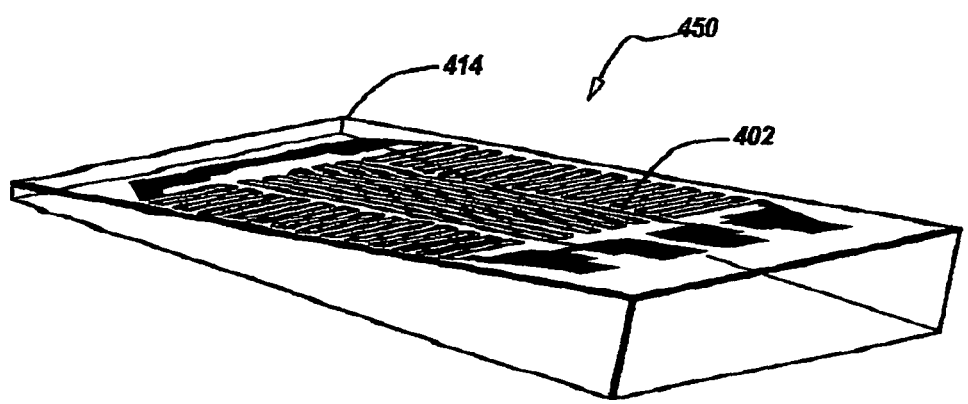
FIG. 4D illustrates an exemplary sensor mounted on a tapered surface according to an exemplary embodiment of the present invention.
Figure 5:
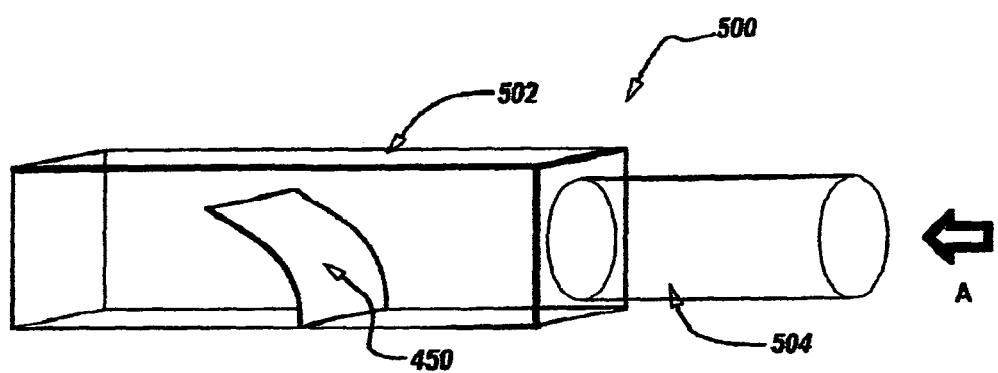
FIG. 5 is a perspective view of a device that captures spirometry data and breath sounds simultaneously according to the teachings of the present invention.
Figure 6A:
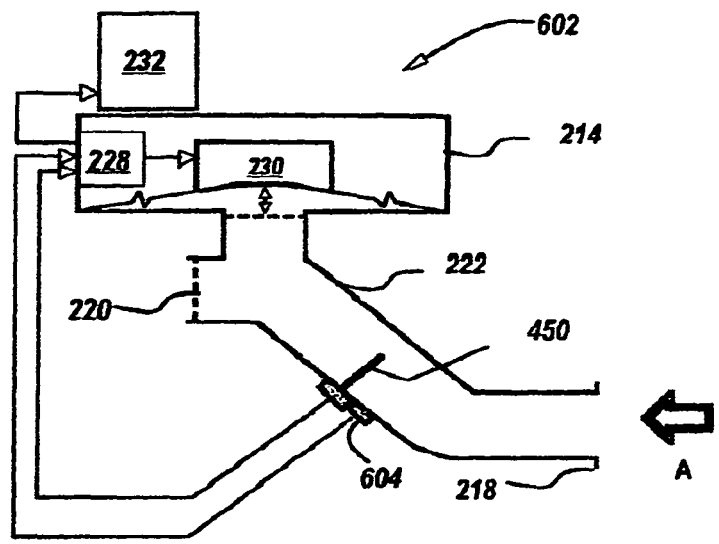
FIG. 6A is a schematic depiction of an exemplary FOT or IOS device that employs a piezoresistive airflow sensor and a pressure sensor according to the teachings of the present invention.
Figure 6B:
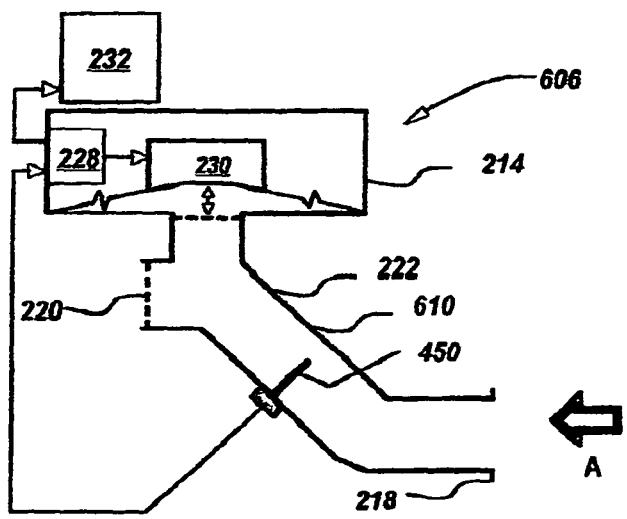
FIG. 6B is a schematic depiction of another exemplary FOT or IOS device that employs only the piezoresistive airflow sensor according to the teachings of the present invention.

FIG. 4D illustrates an exemplary sensor 402 mounted on or affixed to a tapered surface 414 of the flap 450 according to an embodiment of the present invention. The flap 450 formed according to FIG. 4D may be used in a device to detect and/or capture spirometry data and breath sounds simultaneously. Such an exemplary device is illustrated in FIG. 5. The flap 450 may also be used in connection with FOT or IOS devices, as illustrated in FIGS. 6A-6B.

Figure 4E:
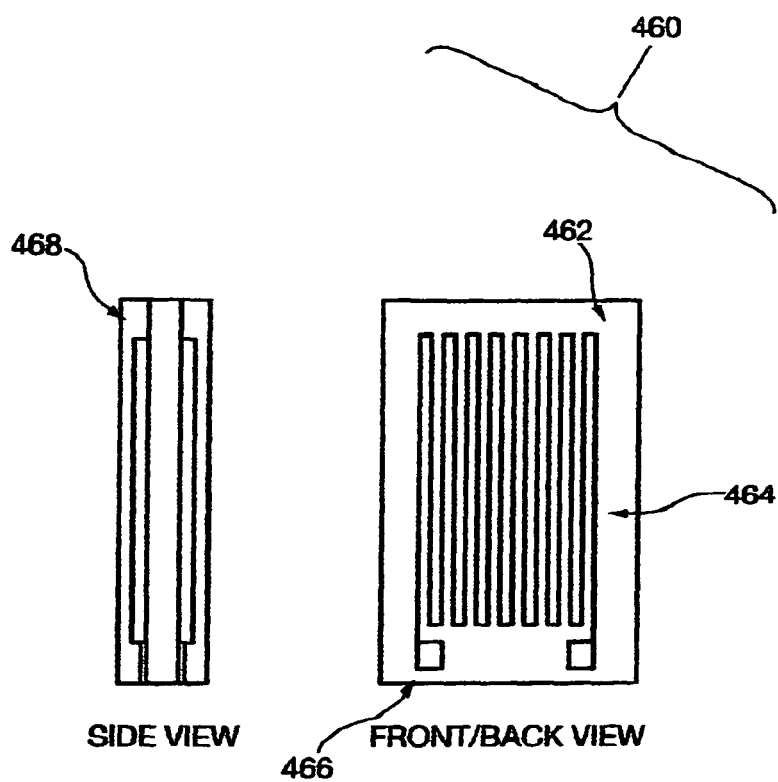
FIG. 4E illustrates an exemplary pair of symmetric sensors mounted on a tapered surface according to an exemplary embodiment of the present invention.

FIG. 4E illustrates an alternative exemplary sensor, in particular a symmetric sensor 460. In this sensor, substrate 462 is coated with metal 464 on both sides of the flap. Coating 468 may then be applied to provide further structural integrity and protection for the deposited metal. Ideally, this sensor is completely balanced, positionally, on the flap substrate, i.e. the metal is deposited symmetrically with regard to side-to-side and front-to-back dimensions. Pads 466 are provided for electrical connection to the sensor. The metal of this sensor may be deposited by any of a number of techniques such as sputtering, e-beam, and thermal evaporation. Symmetric sensors may be more reliable than non-symmetrical sensors, for example where elastic stretching of the flap occurs in response to air pressure, whereby measurement by a single sensor, placed on one side of the flap may be distorted. This is particularly so where multiple axes of stretching and bending of the flap are caused by the airflow. This is so in both the case of using either a single sensor or array of sensors on one side of the flap. Greater accuracy may therefore result with a symmetrical sensor in which the signal from the piezoresistive element(s) on the up-wind side, which are subject to both bending stretch and longitudinal stretch, are compared with signals from a piezoresistive element(s) on the opposite side of the flap, which may not be subject to each and every stretching component. Alternatively, or in combination, the sensed signals from the "back-side" sensor(s) may at least be used to compensate for such stretching through comparative signal analysis.

FIG. 5 illustrates an exemplary airflow sensing device 500 that captures both spirometry data and breath sounds. The device 500 includes an airflow chamber 502 attached to a mouthpiece 504. The airflow chamber 502 is illustrated as a rectangular chamber in FIG. 5 for illustrative purposes only. Those of ordinary skill in the art will readily recognize that the airflow chamber 502 may have any suitable shape, length or size, including but not limited to a circular chamber. The flap 450 includes a thin film sensor 402 and is provided within the airflow chamber 502. As illustrated, the flap 450 is mounted to a wall of the chamber and extends outwardly therefrom into the chamber 502. The flap 450 is positioned so as to be transverse or perpendicular to the direction of airflow, indicated by arrow A.

As illustrated in FIG. 4D, the flap 450 can have a positive or a negative taper. Specifically, the airflow sensing device 500 simultaneously measures the airflow by measuring the displacement of the flap 450 and the sound by measuring the vibration of the flap 450. The device 500 may be used in diagnosing and monitoring lung diseases or conditions that are associated with changes in spirometry values and characterized by abnormal lung sounds.

Figure 7A:
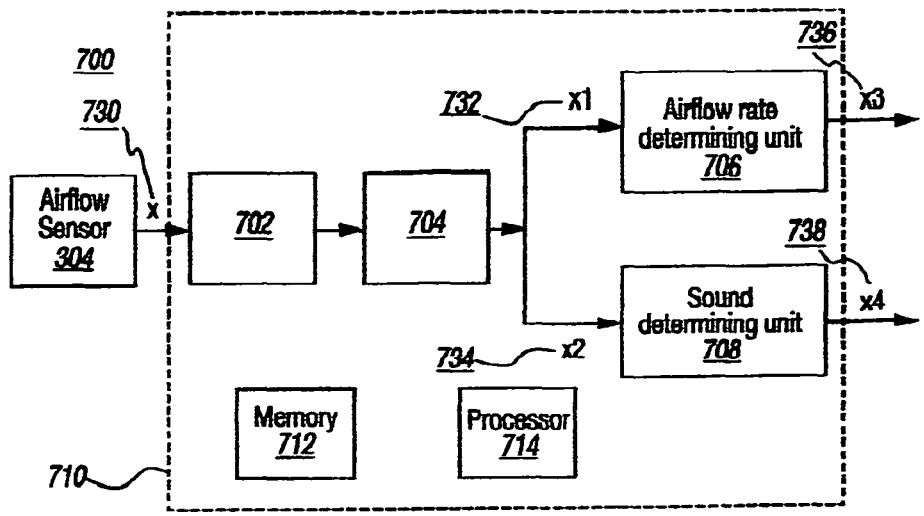
FIGS. 7A-7C are a schematic block diagram of a system where the airflow measuring device of the present invention is used to gather and analyze spirometry data and breath sounds simultaneously.
Figure 7B:
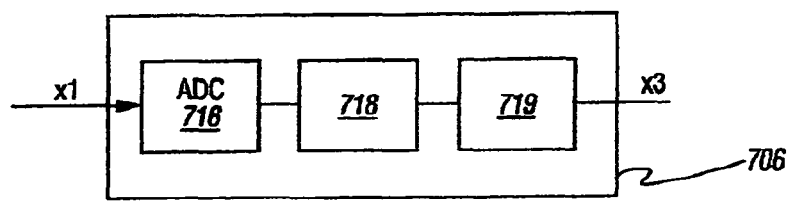
Figure 7C:
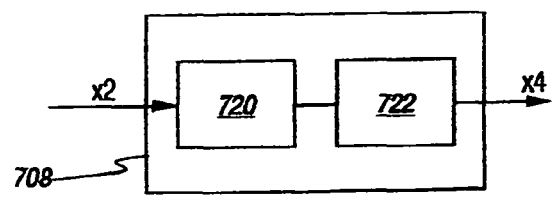

According to an exemplary embodiment, the device 500 may be used by a patient to input the spirometry and auscultation data. The patient breaths into device 500 through the mouthpiece 504. The inhalation or the exhalation of the patient creates an airflow in the direction A illustrated with the arrow in FIG. 5. The airflow displaces and vibrates the flap 450 in the airflow chamber 502. The displacement and the vibration of the flap 450 are sensed by the sensor (not shown) provided on the flap 450. The sensor generates an output signal that represents data associated with the displacement and the vibration of the flap 450. The data associated with the displacement of the flap 450 is used to measure airflow characteristics for spirometry analysis. The data associated with the vibration of the flap 450 is used to measure breath sound characteristics for auscultation analysis. The processing of the output signal is illustrated in FIGS. 7A-7C and is discussed below.

As indicated above, the flap 450 of the present invention may also be used in connection with FOT or IOS devices, as illustrated in FIGS. 6A-6B. FIG. 6A illustrates an airflow sensing device 602 for FOT or IOS applications. The sensing device 602 includes an exemplary piezoresistive sensor 304 according to an embodiment of the present invention. The piezoresistive sensor is coupled to the flap 450 and is similar to the flap 450 illustrated in FIGS. 4D and 5. The piezoresistive sensor 304 replaces the pneumotachometer 216 and the flow transducer 224. Pressure transducer 604 may employ different technology than pressure transducer 226 of the conventional FOT or IOS device 206.

The piezoresistive sensor 304 of the present invention functions as one branch of the Wheatstone bridge from which the voltage output feeds into an analogue-digital converter incorporated into the digital signal processor 228. The digital signal processor 228 may also include the Wheatstone bridge and amplifiers. The piezoresistive sensor-based FOT or IOS device 602 is capable of the full range of measurements that can be performed with the conventional FOT or IOS device 206. In addition, according to various embodiments of the present invention, the piezoresistive sensor-based FOT or IOS device 602 is capable of measuring impulse frequencies greater than 50 Hz, for example frequencies up to 1000 Hz. The piezoresistive sensor-based FOT or IOS may measure impulse frequencies between about 1 Hz and about 1000 Hz. More preferably, the piezoresistive sensor-based FOT or IOS may measure frequencies of between about 35 Hz and about 1000 Hz. The piezoresistive sensor-based FOT or IOS device 602 is less expensive to build and maintain, more rugged and portable, easier to clean, and simpler to operate than the conventional FOT or IOS device 206.

According to an illustrative example, the FOT or IOS device 602 may be used by a patient for collecting data for FOT or IOS applications. The patient may breath through the mouthpiece 218 provided at one end of the FOT or IOS device 602. The breathing generates airflow in the direction of the arrow A, as illustrated in FIG. 6A. The flap 450 including the sensor 304 of the present invention is provided in a direction substantially perpendicular to the direction of the airflow. The airflow causes the flap 450 to move and vibrate. The sensor 304 provided on the flap 450 senses the movement, i.e. displacement, and vibration of the flap 450. The sensor 304 generates an output signal that is representative of the displacement data and the vibration data of the flap 450. The displacement data is correlated with the airflow characteristics, such as airflow rate, of the airflow. The vibration data is correlated with the breath sound characteristics associated with the airflow. The output signal of the sensor 304 is then sent to digital signal processor 228 and a computer 232 for further processing. The processing of the output signal is discussed below in connection with FIGS. 7A-7C. FOT or IOS device 602 also includes a pressure sensor 604 that collects pressure data generated by the airflow. The pressure data is also sent to the computer 232 for processing. The pressure data collected by the pressure sensor 604 may be used for calculating impedance of the respiratory flow.

According to various embodiments of the present invention, the sensor 304 of the present invention may be used to measure the response of the airway to perturbations other than the series of short pressure pulses used in IOS and continuous waves in FOT.

Figure 1:
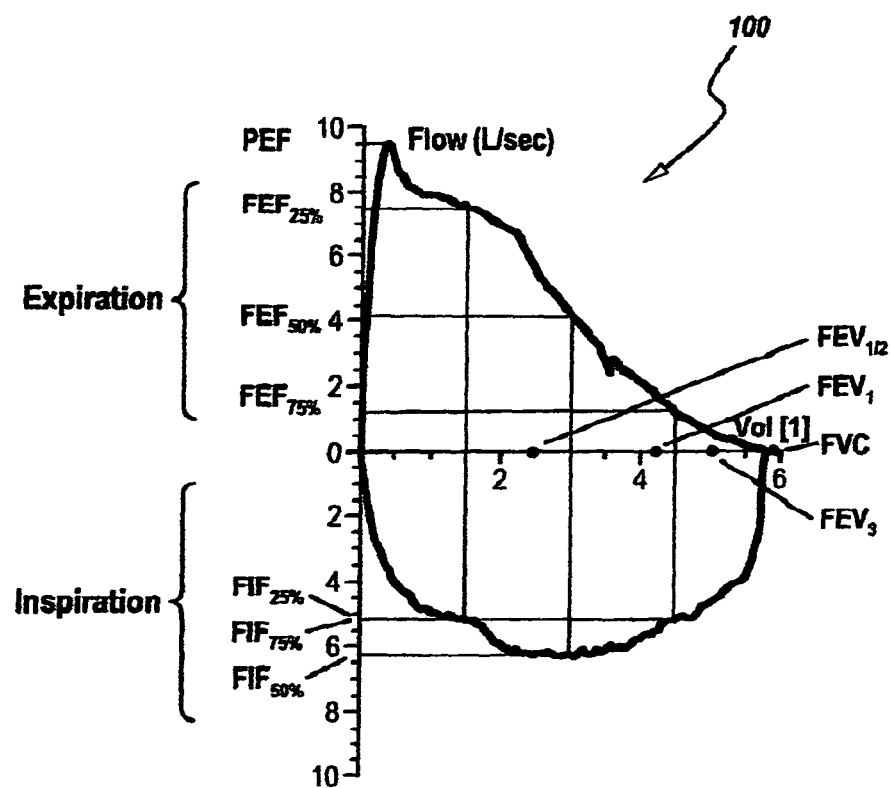
FIG. 1 is a graphical depiction of a conventional spirometry flow-volume loop.
Figure 2A:
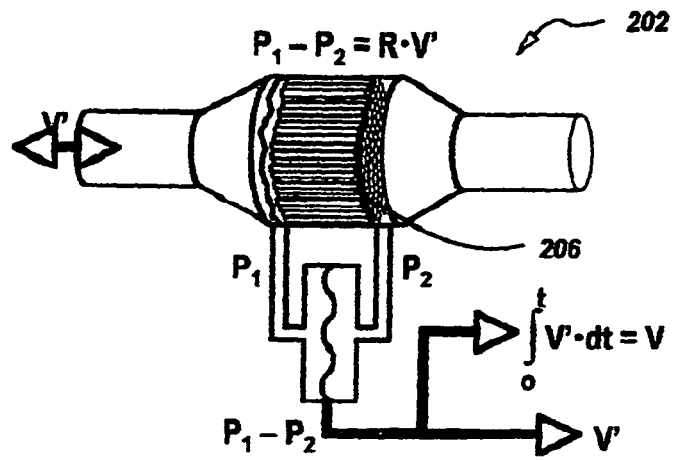
FIG. 2A is a schematic view of a conventional Fleisch-type pneumotachometer.
Figure 2B:
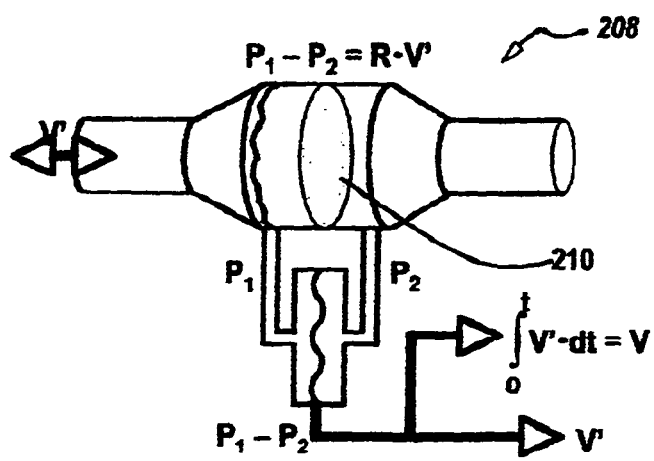
FIG. 2B is a schematic view of a conventional Lilly-type pneumotachometer.
Figure 2C:
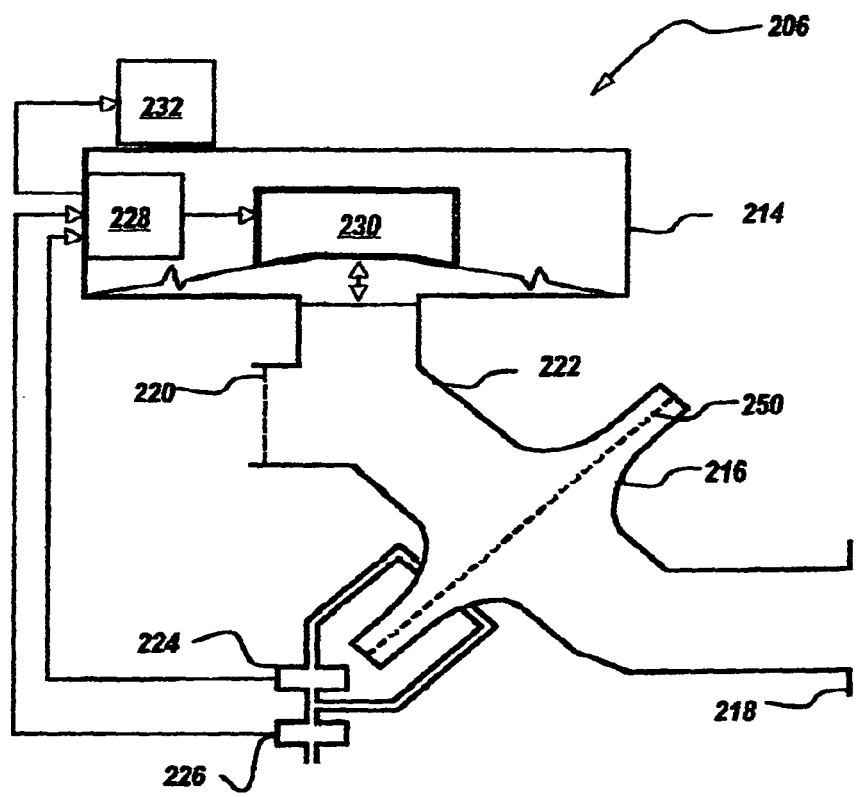
FIG. 2C is a schematic view of a conventional device for performing FOT or IOS techniques.

The sensing device 606 illustrated in FIG. 6B is a simpler version of the device 602 illustrated in FIG. 6A in that it does not include the pressure sensor 604. The piezoresistive sensor 304 of the FOT or IOS device 606 may detect airflow velocity and, therefore, differences in pressure. Accordingly, the impedance of the respiratory flow may be calculated using the data from the piezoresistive sensor 304 provided in the FOT or IOS device 606. In the sensing device 606, the pressure may be measured using the sensor 304. That way, the sensing device 606 is capable and adapted to measure the impedance inside the airway 610, for example at a central point of the airway 610. The measurement of impedance is more accurate when the measurement is taken at a location closer to the air source. Accordingly, the sensing device 606 of FIG. 6B may provide better and more accurate measurements compared to the device 206 illustrated in FIG. 2C.

The FOT or IOS device 606 can be used for the calculation of impedance of the spontaneous breathing and the superimposed impulse signal. Using the FOT or IOS device 606, it is possible to determine the phase, frequency, and signal strength at two physical points, i.e. the sensor 304 and the loudspeaker 230. The sensor and/or the flap 450 may contain additional elements such as additional parallel and/or perpendicular strain gauge sensor 402. The additional elements of the sensor 304 may detect additional data streams from detectors such as flexible membrane pressure sensors.

According to an illustrative example, the FOT or IOS device 606 may be used by a patient for collecting data for FOT or IOS applications. The patient may breath through the mouthpiece 218 provided at one end of the FOT or IOS device 606. The breathing generates airflow in the direction of the arrow A, as illustrated in FIG. 6B. The flap 450 including the sensor 304 of the present invention is provided in a direction substantially perpendicular to the direction of the airflow. The airflow causes the flap 450 to move and vibrate. The sensor 304 provided on the flap 450 senses the movement, i.e. displacement, and vibration of the flap 450. The sensor 304 generates an output signal that is representative of the displacement data and the vibration data of the flap 450. The displacement data is correlated with the airflow characteristics, such as airflow rate, of the airflow. The vibration data is correlated with the breath sound characteristics associated with the airflow. The sensor 304 of the FOT or IOS device 606 may also sense a pressure differential caused by the airflow. Therefore, the output signal of FOT or IOS device 606 may also represent the pressure data associated with the airflow. The output signal of the sensor 304 is sent to digital signal processor 228 and a computer 232 for further processing. The processing of the output signal is discussed below in connection with FIGS. 7A-7C.

According to various embodiments of the present invention, the piezoresistive circuits 404 and 406 may be used in combination for phase calibration allowing quadrature detection. Semiconductor pressure sensors may also be incorporated in the base of the sensor 304 that may be used for reference.

FIG. 7A illustrates an exemplary sensing system 700 where the sensor 304 of the present invention is used to gather and analyze spirometry data and sound data associated with the airflow simultaneously. The sensor 304 outputs a signal x 730 that represents two sets of data simultaneously, i.e. the spirometry data x1 (732) and the sound data associated with the airflow x2 (734). The output x of the sensor 304 is sent to a voltage conversion unit 702. According to an embodiment of the present invention, the voltage conversion unit 702 may be a Wheatstone bridge. The output of the voltage conversion unit 702 is then sent to an amplification unit 704, such as an amplifier. The output of the amplifier represents two sets of converted and amplified data, i.e. the spirometry data x1 (732) and the sound data associated with the airflow x2 (734).

The spirometry data x1 (732), i.e. the displacement of the flap 450 carrying the sensor 304, may be provided to an airflow rate determining unit 706. The output x3 (736) of the airflow rate determining unit 706 represents the airflow data, i.e. the spirometry data. The sound data x2, i.e. the vibration of the flap 450 carrying the sensor 304, may be provided to a sound determining unit 708. The output x4 of the sound determining unit 708 represents the sound data, i.e. the auscultation data. The airflow determining unit 706 and the sound determining unit 708 may be a part of a determining unit 710. The determining unit 710 may include a processor 714 for performing various computations and analysis using the output x of the sensor 304. The determining unit 710 may also include a memory 712 for storing the airflow data, the sound data and/or the results of the analysis performed on the airflow data and/or the sound data. The determining unit can include other circuitry or components as would be obvious to one of ordinary skill in the art.

FIG. 7B illustrates the airflow rate determining unit 706 of FIG. 7A. The airflow rate determining unit 706 includes an analog-to-digital converter (ADC) 716. The spirometry data x1, typically an analog signal, is input to the ADC 716. The output of the ADC 176 is a DC voltage that may be coupled to a calculation unit 718. The calculation unit 718 correlates the input data signal with a pre-determined calibration curve to determine the airflow rate. The calculation unit 718 generates graphical representations of the input data and/or the results of correlating the input data with the pre-determined calibration curve. These results can be displayed on an associated display device (not shown), or can be stored in memory 712.

FIG. 7C illustrates the sound determining unit 708 of FIG. 7A. The sound determining unit 708 includes a sound processing unit 720. According to various embodiments of the present invention, the sound processing unit 720 may be a sound card. The sound data x2 is input to the sound processing unit 720. The output of the sound processing unit 720 is a sound data signal representative of the sound generated by the source of the airflow (i.e., the patient). The sound data signal is then passed through a frequency conversion unit 722. The frequency conversion unit 722 may apply Fast Fourier Transform (FFT) technique to the sound data signal. The output from the frequency conversion unit 722 may be used to determine peak frequencies that are representative of medical conditions. Accordingly, using the output of the frequency conversion unit 722, it is possible to determine whether a patient has a medical condition, such as asthma and the like.

Figure 8A:
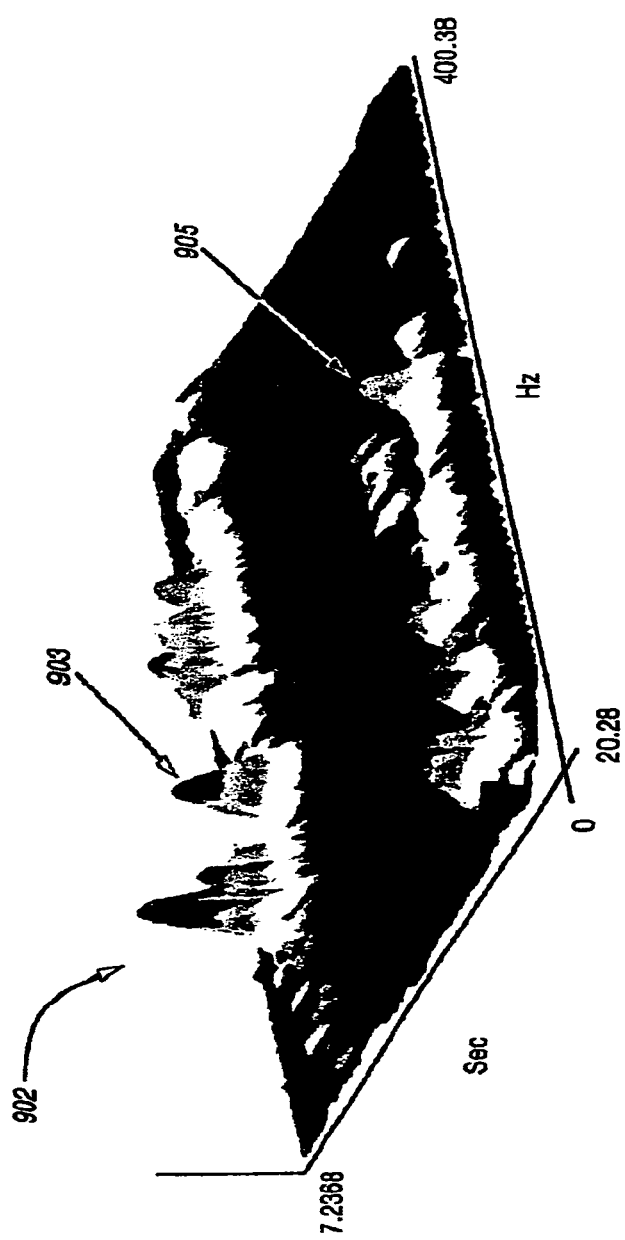
FIG. 8A illustrates an exemplary three dimensional plot representing auscultation data gathered using the airflow measuring device of the present invention.
Figure 8B:
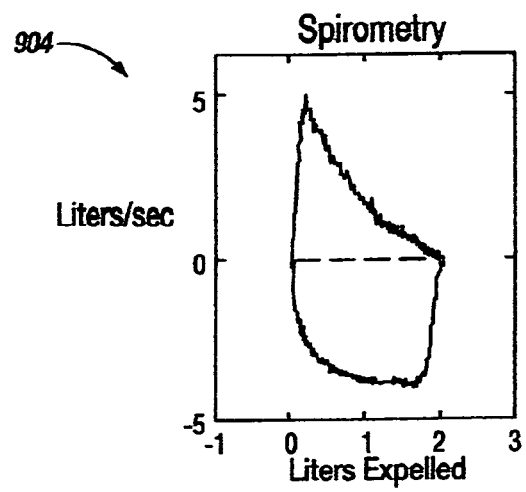
FIG. 8B illustrates an exemplary spirogram representing spirometry data gathered using the airflow measuring device of the present invention.
Figure 8C:
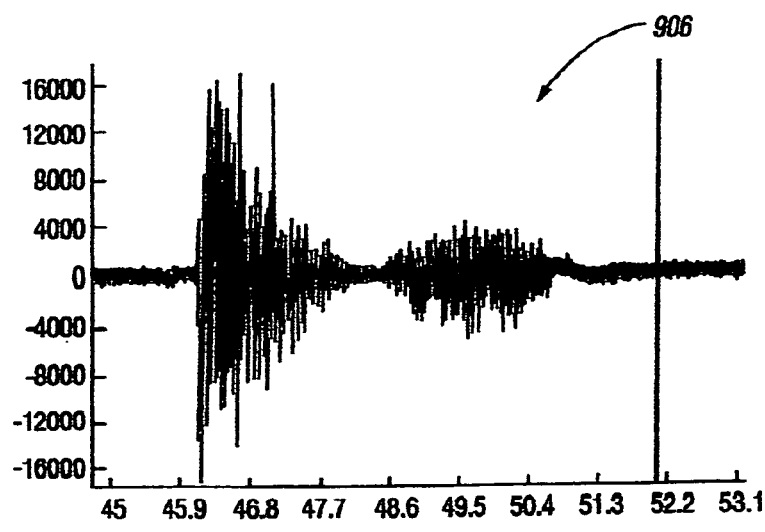
FIG. 8C illustrates expiratory and inspiratory recordings from a sound card according to an exemplary embodiment of the present invention.

The output of the airflow rate determining unit 706 and the sound determining unit 708 (736 and 738 respectively) may be visually represented. FIGS. 8A-8C illustrate various way of visually representing the spirometry data and the sound data detected and/or measured using the airflow measuring device 500 of the present invention. An adult male is used as a subject to collect the data illustrated in FIGS. 8A and 8B. FIG. 8A illustrates the auscultation data and FIG. 8B illustrates the spirometry data, both simultaneously measured using a single airflow sensor.

FIG. 8A illustrates a three dimensional plot 902 of frequency, time and auscultation data of an adult male subject. A Fast Fourier Transform may be performed on the auscultation intensity data. The airflow sensor of the present invention is a bidirectional sensor, i.e. the sensor of the present invention may measure both the inhalation and exhalation data. Accordingly, both the inhalation data 903 and the exhalation data 905 are represented on the three dimensional plot 902 of FIG. 8A.

FIG. 8B illustrates the spirogram 904 of the adult male subject. The data illustrated on FIG. 8B may be collected using the same airflow sensor used to detect the data illustrated on FIG. 8A. It is also possible to record the breath sound data at the output of a sound card. FIG. 8C illustrates expiratory and inspiratory recordings 906 from the sound card.

Figure 9A:
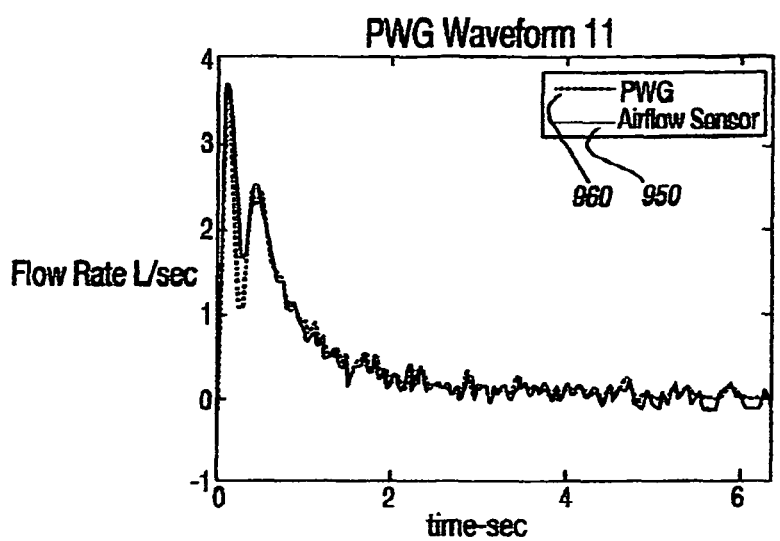
FIGS. 9A-9B is a graphical depiction showing a comparison between data gathered using an airflow sensor according to the teachings of the present invention and simultaneous data gathered using a conventional Pulmonary Waveform Generator (PWG)
Figure 9B:
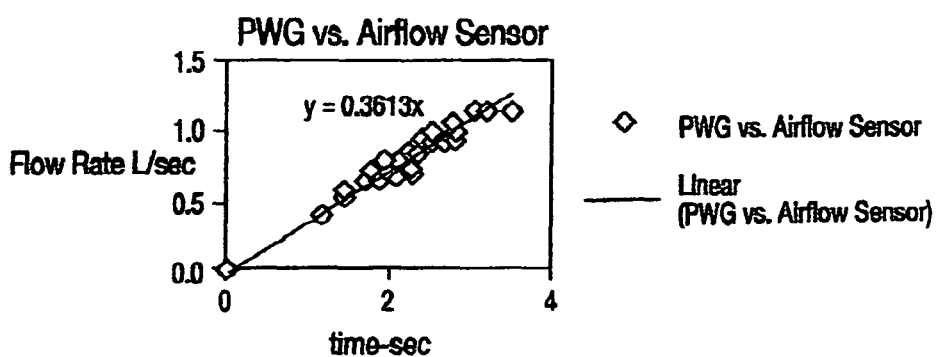

The airflow sensor of the present invention is tested with various applications. The American Thoracic Society publishes spirometry waveforms for the purpose of spirometer calibration and validation of accuracy. These waveforms are fed from a computer into a pulmonary waveform generator (PWG) consisting of a computer-directed servo-controlled pump which generates airflow according to those patterns, which a spirometer can then be tested for its ability to track. FIGS. 9A and 9B compare the standard pulmonary waveform #11 output of a PWG with the recording by the airflow sensor of the present invention. In FIGS. 9A-9B, the data 950 gathered using an exemplary airflow sensor of the present invention are compared to the standard pulmonary waveform #11 data 960 of the PWG.

FIG. 9A illustrates the response of the airflow sensor according to the present invention versus the observed and calibrated PWG curve. The PWG curve is characterized by two initial humps followed by a decay. As illustrated in FIG. 9A, the sensor of the present invention provides data that match well with the output of the PWG.

FIG. 9B shows a comparison of peak expiratory flow $(PEF)^{1/2}$ from the PWG data set versus the maximum voltages obtained from the airflow sensor of the present invention. As illustrated, a linear correlation is observed.

Figure 10:
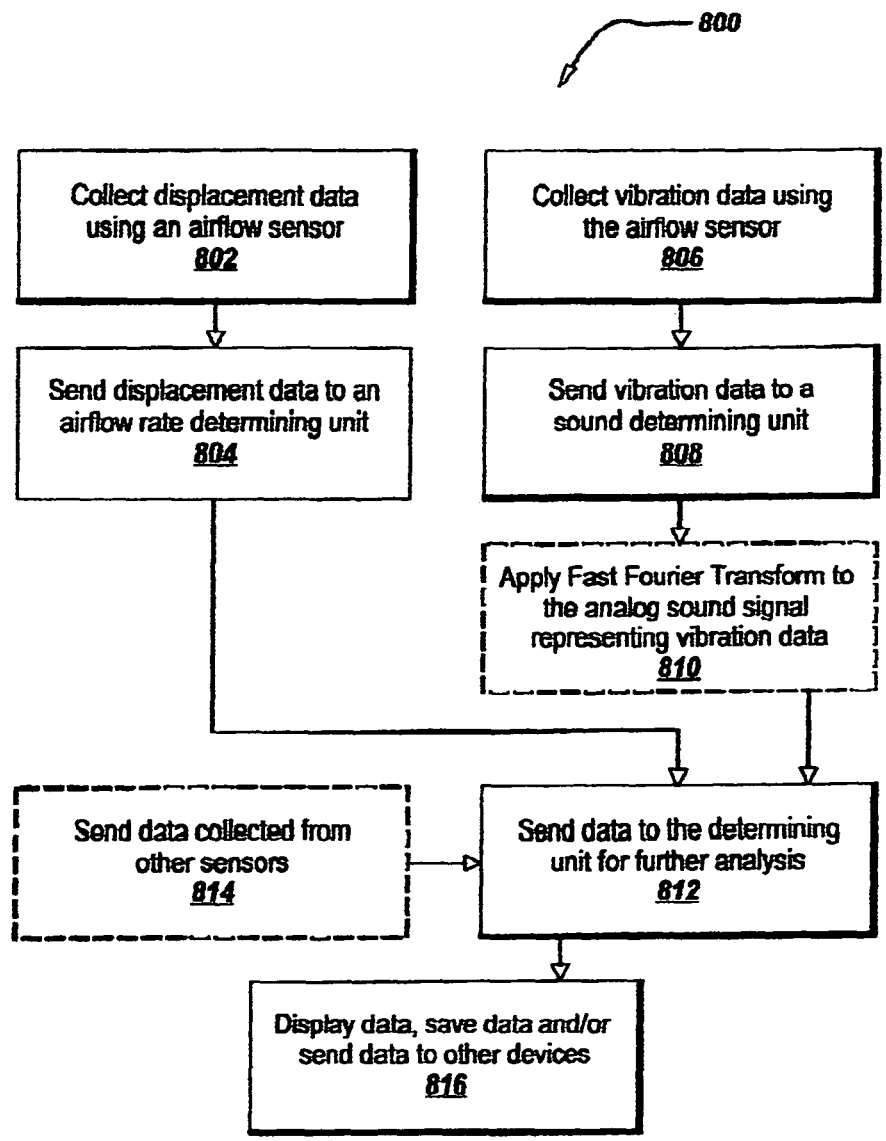
FIG. 10 is a flowchart of steps illustrating an exemplary method of simultaneously gathering spirometry and auscultation data using the airflow sensor of the present invention according to an exemplary embodiment of the present invention.

A flowchart 800 of steps illustrating an exemplary method of simultaneously gathering spirometry and auscultation data using the airflow sensor of the present invention is provided in FIG. 10. The method includes collecting displacement data using a sensor according to the present invention (step 802). The displacement data relates to the displacement of the flap including the sensor caused by the airflow generated by a source. The displacement data may be used to measure the airflow rate of the source, such as a patient. The displacement data may be used as the spirometry data. According to various embodiments of the present invention, the displacement data is sent to an airflow rate determining unit (step 804). The airflow rate determining unit may include an analog-to-digital converter.

The method further includes collecting vibration data using the same sensor of the present invention (step 806). The vibration data relates to the vibration of the flap including the airflow sensor caused by the airflow generated by the source. The vibration data may be used to measure the sound of the source. The vibration data may be used as the auscultation data. The vibration data is sent to a sound processing unit (step 808). The sound processing unit may include a sound card. Accordingly, the method collects two sets of data, i.e. displacement data and vibration data, using the same sensor.

The use of a thin film flexible polymeric in the present invention allows modal vibrations to be used as a mechanism for representing sound. Any physical object subjected to a force that allows slippage, whether it be a flute subjected to airflow slipping across its mouthpiece or a violin with a bow slipping over a string, will have resonance modal vibrations that are activated when the applied force meets specific physical conditions. When specific air velocities are achieved with the elastic flap sensor of the present invention, resonance conditions are satisfied and the timing, frequency and energy of the resulting sonic vibrations can be quantified if the data set is converted by such analytic modalities as Fast Fourier Transform algorithms.

Accordingly, in step 810 of the flowchart 800 of FIG. 10, a Fast Fourier Transform or other algorithms may be applied to the analog sound data signal representing the vibration data in order to decompose the sequence of values collected by the airflow sensor into components of different frequencies for further analysis (step 810). The result of the Fast Fourier Transform and/or the raw data collected by the airflow sensor is sent to a determining unit for further analysis (step 812) and visual representation (step 816). If additional data are collected by other sensors (step 814), such as chemical sensors or thermal sensors, used in conjunction with the airflow sensor of the present invention, the additional data may also be sent to the determining unit to be analyzed along with the displacement and vibration data (step 812). When the collected data are analyzed using the determining unit, the data may be visually displayed, saved, or sent to other devices (step 816).

In actual use, the airflow sensor provided herein and shown in FIGS. 5-6 has revealed certain non-linear response characteristics attributable to the physical and chemical composition of the flap. These non-linear characteristics reveal themselves in the actual voltage readings from the flap-mounted sensor. To test the ideal flap response characteristics, square and/or rectangular wave input profiles may be used to drive the flap and sensor after which the output response of the flexible strain gauge may be studied and analyzed. Based on these tests, as described below, algorithms have been developed to correct for certain non-linear characteristics in the output data from the sensor. These algorithms may be programmed in software, stored in memory and may run on any of the numerous processors contained in the overall airflow measurement system of FIGS. 5 and 6. Examples of suitable locations for such processing are the computing device 306 of FIG. 3 or the post processing unit 719 within the determining unit 706 shown in FIG. 7B. Alternatively, the algorithms may be included in something as close to the sensor as semiconductor silicon on the strain gauge sensor itself or in something as removed from but coupled to the sensor such as an accompanying computer setup in which software residing on a computer external to the entire strain gauge is used to collect and analyze the data.

Those of skill in the art will realize that the non-linear characteristics described herein are those that have been detected as of the date of this application and which have been deemed significant enough to require correction. Additional non-linear characteristics may be present which may be identified later and for which correction may be desirable. The apparatus and methods disclosed herein are expected to be applicable to any such later-detected non-linear flap response. In this regard, and despite the determinative nature of the two identified non-linear characteristics disclosed below, it has been determined that empirical testing and corresponding determination of correction functions for the sensor responses are the simplest, most accurate and most cost effective method of generating such correction functions. In further support of this, it should be realized by those of skill in the art that a number of flap and sensor variables will govern the type, extent and nature of the actual non-linear characteristics of any particular flap and sensor arrangement. In particular, the flap and sensor geometry, size, chemical composition, placement with the flow sensing system, and arrangement with respect to one another are some of the many factors affecting the output sensor data and the correction functions needed to accommodate the same.

Two different non-linear flap response characteristics have been identified and isolated as described herein. For these two, algorithms have been developed to compensate for the non-linear response characteristics. The first non-linear characteristic is an exponential decay function associated with an initial incident pulse upon one side of the flap. The second non-linear characteristic is a baseline movement in the flap data most likely attributable to the polymer creep of the Kapton® flap used in the testing of the present invention. These two corrections are the result of two different physical processes that occur simultaneously during a flap response experiment: the bending of the flap due to airflow across it (both directions) and the stretching of the flap under tension due to the streaming of fluid over surface of the flap. Both processes need to be understood in order to fully understand the response function.

Figure 11:
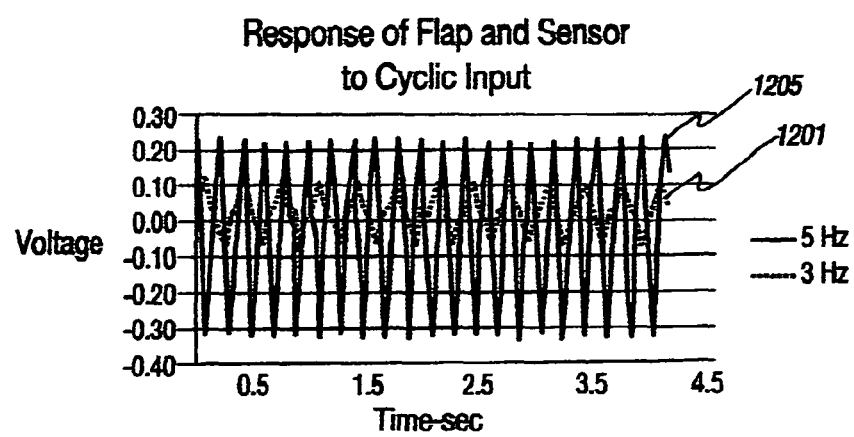
FIG. 11 shows two airflow sensor output responses according to a testing of the present invention.

FIG. 11 provides two unfiltered sensor output responses to an input sinusoidal signal, one at 5 Hz 1205 and one at 3 Hz 1203. At these frequencies, there is no apparent baseline drift and the responses in the middle of the testing show a steady state mode of operation that does not generally require connection. The voltage on the left axis represents the voltage from the determination unit as amplified and normalized by the post reading processing performed by the present invention.

Figure 12:
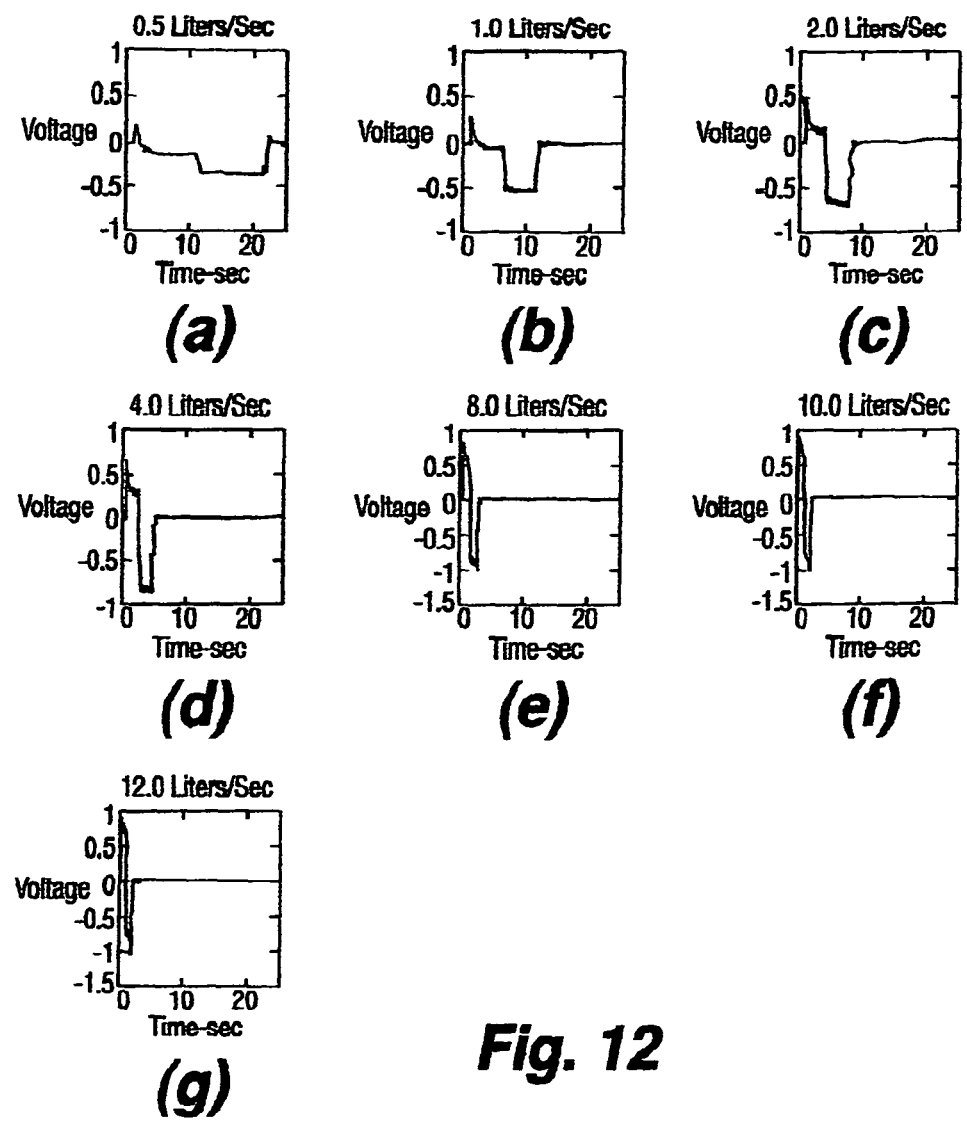
FIG. 12($a$) through 12($g$) show a series of sensor response profiles generated in response to test flow pulses according to one aspect of the present invention.

At lower frequencies of operation, or more particularly in response to single cycle square wave pulses, the voltage output response of the sensor shows a bit more variation; variation that requires correction to maintain fidelity in the flap's output response function. FIGS. 12(*a*)-(*g*) show a series of sensor voltage response profiles generated in response to input rectangular or square-wave air flow impulses. These pulses have both positive and negative components and have been applied to the flap using a pulse waveform generator (PWG). Pulse volumes of 0.5 L/sec, 1.0 L/sec, 2.0 L/sec, 4.0 L/sec., 8.0 L/sec. and 12 L/sec. were used for testing. The pulse periods were selected to be inversely related to the plateau air velocity so as to accommodate the fixed maximum volume of the PWG. The most interesting characteristic of the response is shown in the difference between the two halves of each periodic response profile depending on whether the pulse was a positive pulse (i.e. pushing the flap away from the higher pressure input air pulse) or a negative pulse (i.e. pulling the flap toward the lower pressure input air pulse). The differences in the response profile are consistent and appear to be independent of pulse magnitude or frequency. Nonetheless, the two sides of the pulse response may be independently examined and are labeled as the exponential side and the mesa side. These labels refer to the observed shape of the response functions of the sensor when it is bent away from a positive input fluid pulse. The sensor is not inherently symmetric and does not possess a plane of symmetry parallel to the plane of the thin film sensor itself. The side of the asymmetric sensor being compressed governs both the sign (positive or negative) of the overall signal as well as the need for second order correction functions. It will be recognized by those of skill in the art that the sign of the voltage signal is dependent on other experimental factors such as the exact wiring of the amplifier and that the observed direction of the response (positive or negative response) is not an inherent property of the flap. Once a convention and apparatus is established, the observed response can be used to distinguish the "mesa" vs "exponential." It is unknown, at present, which parameters determine a mesa side or an exponential side of the flap, e.g. sensor placement, sensor composition etc. However, it has been determined that a mesa side response and an exponential side response are always present in a complementary fashion when a full square wave having both positive and negative pulses is input to the flap and sensor.

Figure 13:
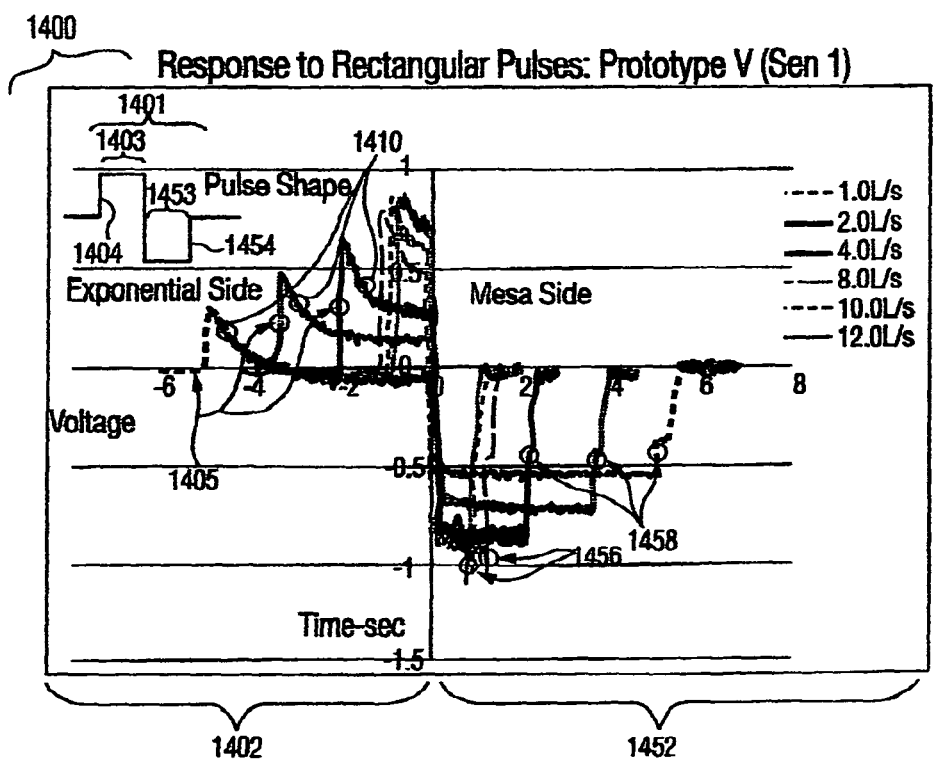
FIG. 13 provides a summation of the sensor responses of FIGS. 12($a$) through 12($g$)

FIG. 13 shows a graph 1400 on which the pulse responses from FIG. 12 are all superimposed and viewed together. The incident test pulse shape 1401 is shown in the upper left hand corner of the plot 1400 and contains positive pulse portion 1402 and negative pulse portion 1453. A few points to be noted include: a) the incident edge of the positive test pulses 1404 produce sharp sidewalls on the positive pulse side response function 1405; b) there is a spike 1456 in the negative pulse side response function 1452 upon release of the input negative pulse 1454; and c) there is a physical kink 1458 in the sidewall response function on the negative response slope upon release of the input negative pulse. The exact cause and nature of some of these non-linear responses is undetermined at present, but the predominant characteristics of the two sides of the overall response function 1402 and 1452 are well understood and accommodated for by the correction functions of the present invention.

Referring again to FIG. 13, the positive pulse input results in an exponential side flap response containing an exponential decay of the initial signal 410 after a strong initial impulse response to the incident positive pulse. The exponential decay function appears to be the same regardless of the air velocity. There are few anomalies in the data on this side. Analysis of the positive pulse side shows that the sensor voltage rises in response to an impulse of air but then undergoes an exponential decay with a final decay point equivalent to the true baseline. In experiments, this exponential decay appears to be the same regardless of the value of the incident volume. Further, and in the empirical tests analyzed with a Kapton® flap, a single equation characterizing the response for all seven volume samples was determined to be:

$$\text{correction} = \frac{1 - e^{-time/190}}{2.7}$$

Figure 14:
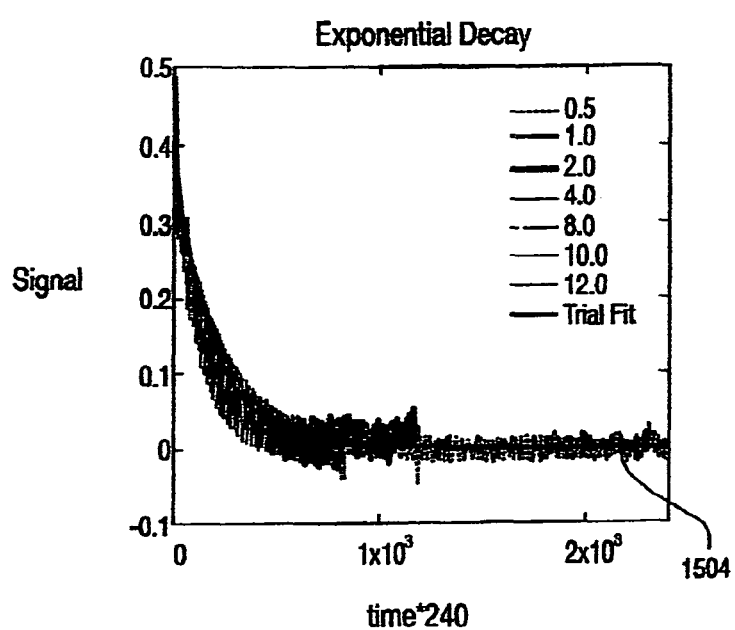
FIG. 14 shows an exponential decay trial function fit according to the exponential decay data provided in one aspect of the present invention.
Figure 15:
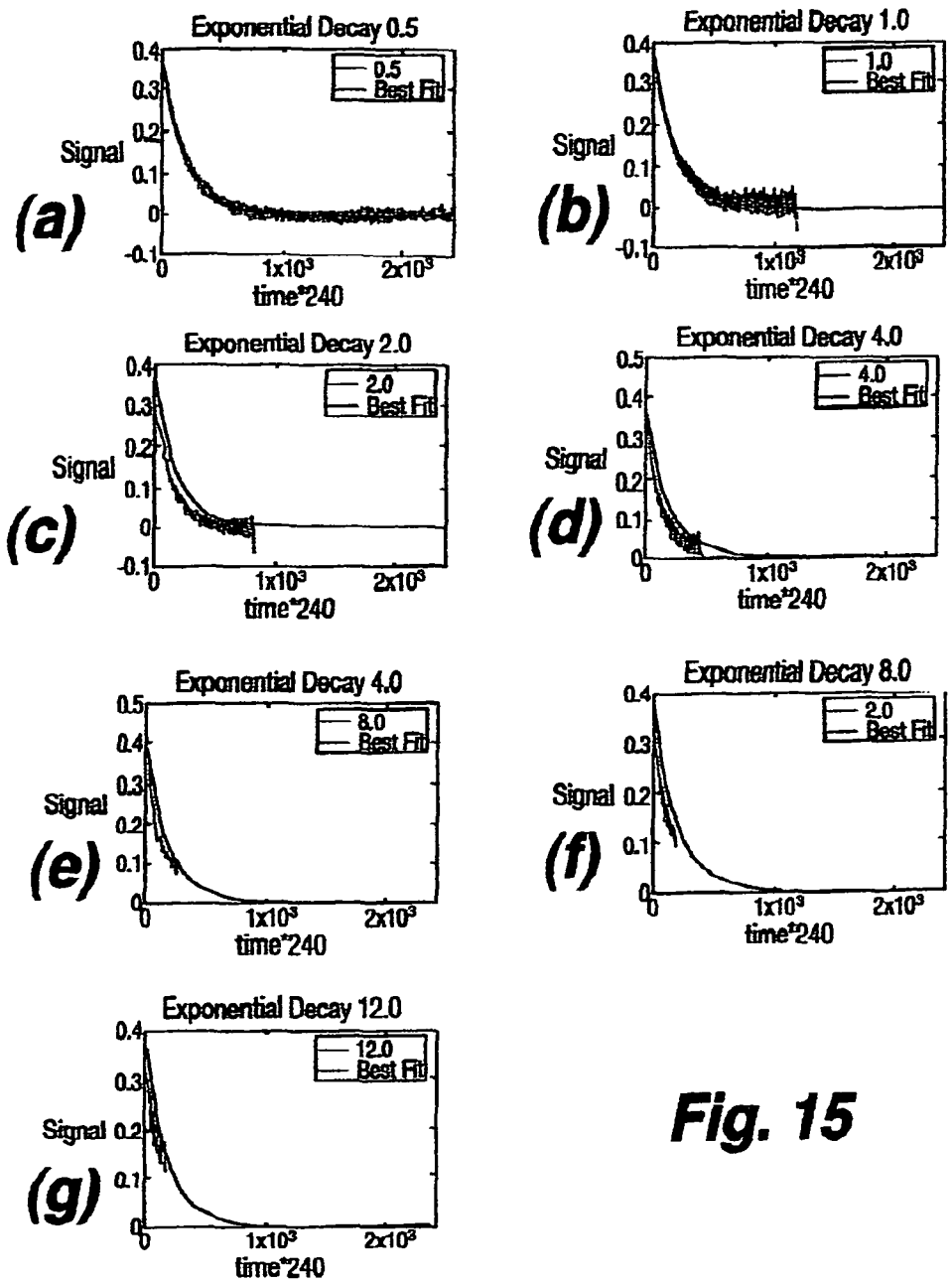
FIGS. 15($a$) through 15($g$) show the raw data for the exponential decays of FIG. 14.

Or more generally by an equation of the form:

$$\text{correction} = \left(a - e^{-\frac{time}{b}}\right)\Big/ c$$

where a, b and c are experimentally determined constants. In this equation, the relevant time for expressing this equation begins at the start of the positive air pulse and lasts until the expiration of the same which is also the start of a negative air pulse at the beginning of the expiratory phase. Exponential decay functions, according to the above-indicated equation, are provided for the particular Kapton® flap tested in FIGS. 14 and 15(*a*)-(*g*). In FIG. 14 in particular, a trial fit function 1504 is provided according to the formula above. Here the above-indicated function harmonizes the response function among the range of test volume data provided and appears to fit the data nicely.

It should be emphasized again, that empirical testing has been used to determine the best error correction so as to fit with and harmonize the actual test data. Therefore the constants provided in the deterministic formula above (i.e. 190 and 2.7) may provide a good fit for certain ranges of operation with the particular flap under test, but may require further correction in other situations, such as with the use of different sensors, flaps or overall flow meter arrangements.

Figure 16:
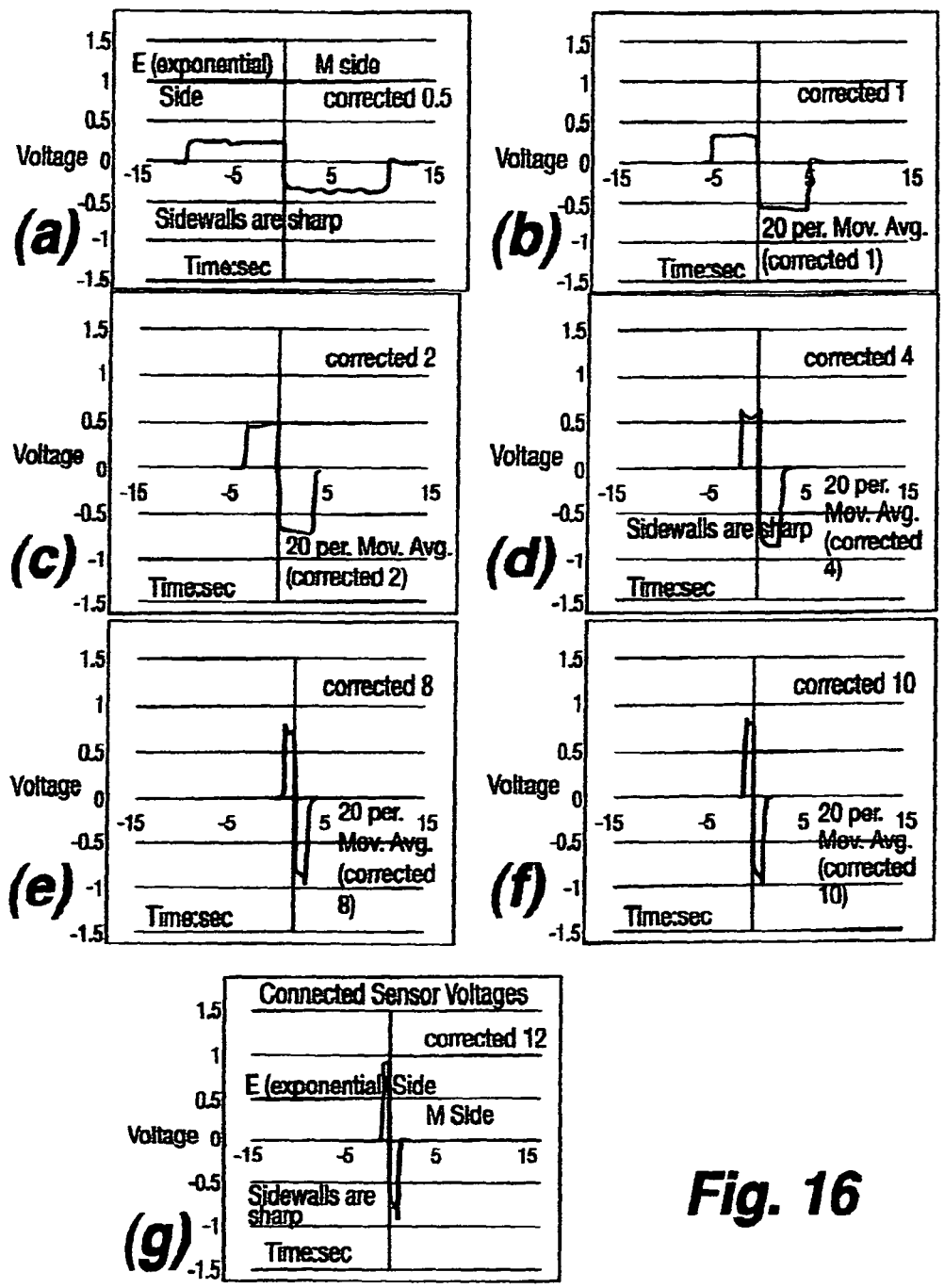
FIGS. 16($a$) through 16($g$) show a series of corrected sensor response profiles from those provided in FIGS. 12($a$) through 12($g$)

When the exponential function provided above was subtracted from the positive portion of the response pulses, certain corrected data is obtained as provided for in FIGS. 16(*a*)-(*f*). It should be noted that the incident exponential side has been corrected for the most part once the exponential function above has been subtracted from the actual response function for that response side.

Figure 17:
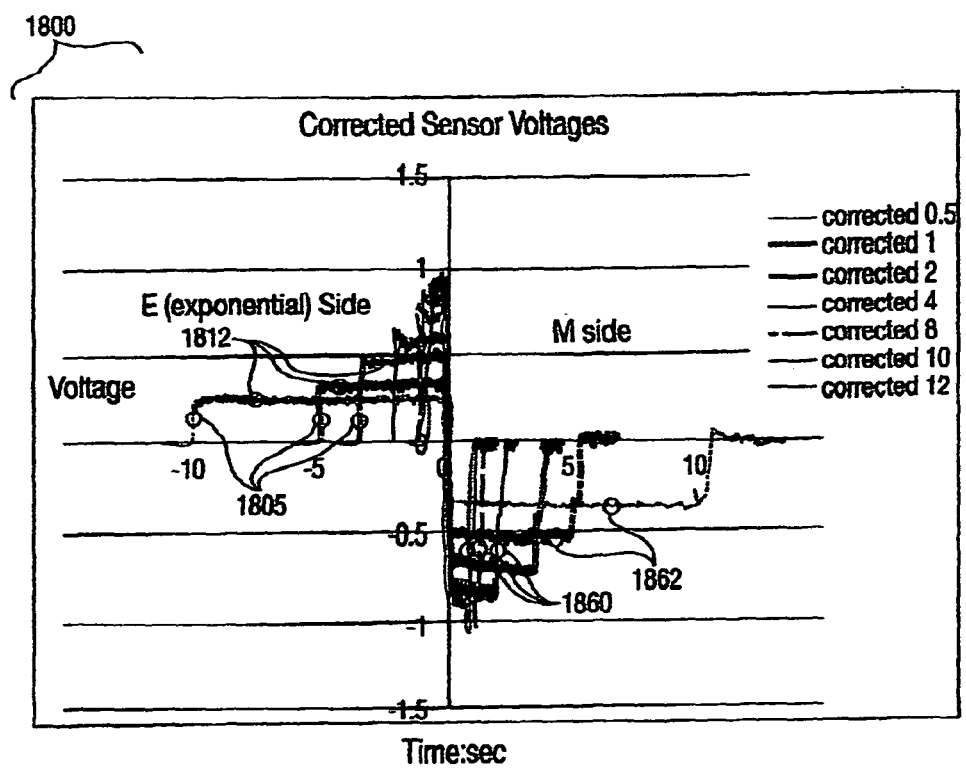
FIG. 17 provides a summation of the sensor responses of FIGS. 16($a$) through 16($g$)

The negative, or mesa, side of the flap response in FIG. 17 contains few non-linear components except for the above-indicated, relatively insignificant "kinks." FIG. 17 shows a graph 1800 in which the pulses responses from FIG. 12, as corrected by the equation above from FIG. 16, are all superimposed and viewed together. In this final summary air flow response graph, a smooth square/rectangular-shaped response function is shown as a final resultant airflow profile produced by the airflow sensor flap that corresponds substantially with the square/rectangular input pulse waveforms presented as inputs to the system. In particular, sharp incident side walls 1805 and sharp terminating side walls 1860 are well defined and the response includes flat plateaus 1812 and 1862 respectively. This side of the flap response function is characterized by linearity and flatness of the plateaus. Even with low airflow rates, such as 0.5 L/s, the response profile is nicely formed and well defined.

Is should be evident to those of skill in the art that other correction functions of varying degree of sophistication and complexity may be employed on the exponential side of the air flap response function to achieve similar results. In particular, a constant function that captures the peak response of the flap at point 412 (FIG. 13) of the incident positive pulse may be used to "square off" the respective portion of the response function. However, while such crude approximations may be acceptable for matching a square wave input impulse, they may result in less precise results than empirically determined functions. The use of simple approximations, in particular, may result in inaccurate interpretation of the response function particularly in the presence of unusual classes of incident waveforms. Again, the present invention is envisioned as employing empirically determined correction functions as the most accurate adjudicators of an accurate presentation of a flap response function that is most true to the input function.

With respect to the second half of the pulse input, the incident test pulse shape 1401 is shown in the upper left hand corner of the plot 1400 and contains positive pulse portion 1402 and negative pulse portion 1453. The mesa side in this particular case 1452 is the response function resulting from the input negative air pulse. It is characterized by linearity and flatness of the plateaus. Again, the sensitivity at low flow rates is notable and the sidewalls are nicely formed.

It can be shown that a sensor constructed in this fashion has excellent sensitivity at low air flow velocities. Further, it has been empirically determined that the sensor response functions may be easily corrected using simple, empirically determined, equations to provide smooth response functions, and in particular accurate response functions to prototypical square wave test inputs. One of the reasons for correcting these response functions is to accurately measure the fluid flow volume through the meter as described below.

FIG. 18(*a*) shows a mesa side response function of the sensor of the present invention to input positive pulses only. The response is shown for two cycles of positive pulses 1902 and 1922. The response is shown for several different test flow rates. Since the output of the piezoelectric sensor is a voltage, a calibration or conversion table must be generated to translate the voltage to flow rates. This is easily accomplished by taking representative plateau points for each volume rate at each cycle, say 1905 and 1925 for the flow rate curve reflecting 4.248 L/sec., 1910 and 1930 for the flow rate curve reflecting 2.9736 L/sec., etc. These data may then be plotted, one curve per cycle, for each cycle's data points on a voltage versus air flow chart as shown in FIG. 18(*b*). This is desirably performed after subtracting out any baseline voltage values, for example the baseline voltage value for the 4.248 L/sec. plot in FIG. 18(*a*) is 1. This can be repeated for each subsequent cycle across all flow rates as desired. As shown in FIG. 18(b), the first two cycles generated from positive pulses on the mesa side of the flap give relatively consistent data curves that allow for easy and consistent conversion between sensor voltage and air flow rates.

FIGS. 19(a) and 19(b) show an equivalently functioning pair of plots for the positive pulses impinging upon the exponential side of the flap. As shown in FIG. 19(b) the correlation of data between cycles 2002 and 2022 is a bit more tenuous since the exponential response function is less defined and consistent. Thus, generating an accurate calibration chart becomes a bit more problematic making the flap side that presents the mesa response function the preferred flap side for measuring incident single directional flow pulses.

Figure 20:
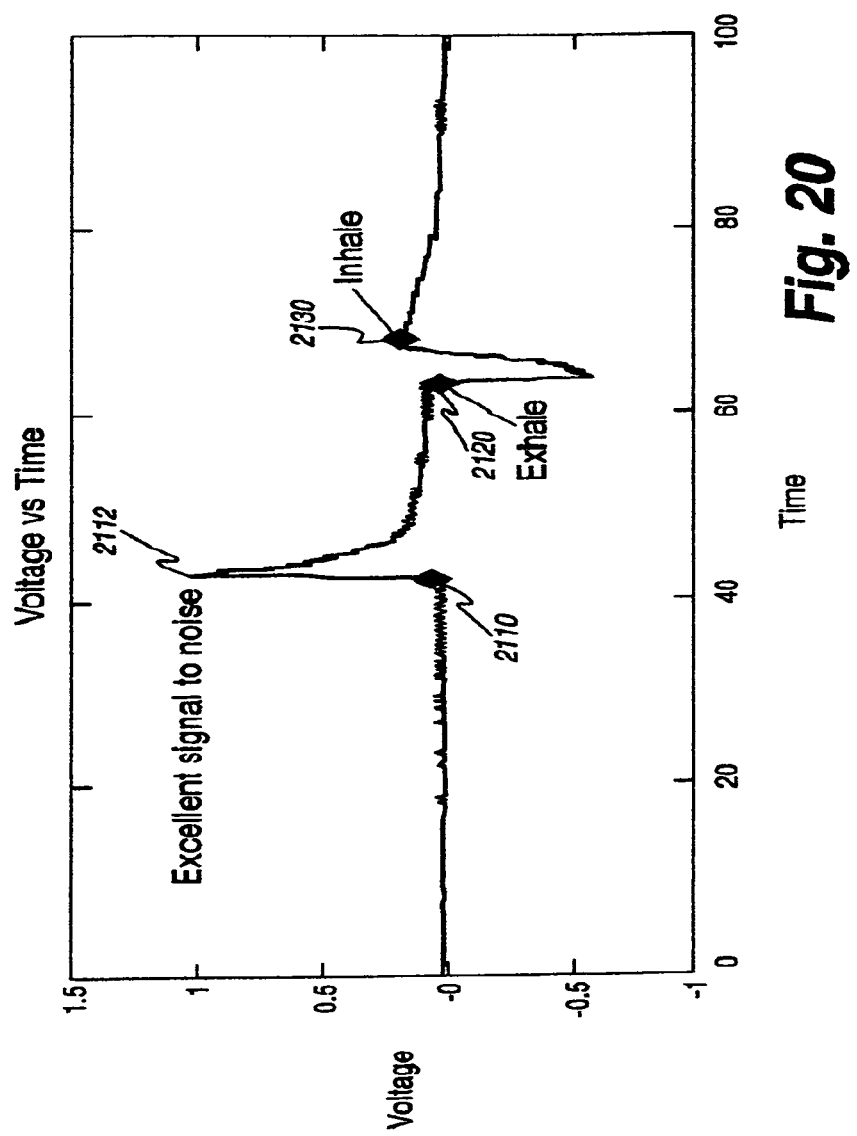
FIG. 20 provides a sensor response of a spirometry profile according to a preferred aspect of the present invention.

To calculate actual flow volumes, the flow rate need only be multiplied by the time period of the flow as measured on the bottom axis of FIGS. 18(a) and 19(a). This is relatively straightforward when nicely defined sensor response functions are available. When the response functions are not so well defined, such as when they're uncorrected, determining the time period of the incident fluid pulse becomes more problematic. FIG. 20 shows a single cycle spirometry response using the sensor of the present invention. The exhale, or positive pulse, is shown to be made on the exponential response side of the flap and sensor, since the initial spike terminating at 2112 decays exponentially. Even the mesa side response for the inhale, or negative pulse, is not very well defined. The difficulty here is determining where the two cycle periods begin and end.

One very simple method of making this determination is to continuously calculate a first order derivative on the voltage data as it is received. The end points of the cycles are then easily determined by the maximum and minimum inflection points (values of the first order derivative). As shown in FIG. 20, point 2110 is a maximum derivative point and marks the beginning of the incident positive pulse. Likewise, point 2120 indicates a minimum inflection point and marks the end of the incident positive pulse—as well as the beginning of the next incident negative pulse presuming that the input is continuous and has no periods of zero pulse input. Subsequently, the next positive inflection point at 2130 marks the end of the incident negative pulse—as well as the beginning of the next incident positive pulse, etc.

As mentioned previously, the second non-linear characteristic is a baseline movement of the flap response that is most likely attributable to the polymer creep of the Kapton® flap used in the testing of the present invention. Those of skill in the material science arts will realize that the polymer backbone of the strain gauge will show a viscolastic stretch when air flows over the surface of the bending flap. Air blowing over the surface of the flap will have a perpendicular component causing the flap to bend and a parallel component causing the flap to extend or be under tension. Regardless of which way the sensor is bent, creep is expected since the flap is stretched when flexed in either direction. While it is observed that polymer creep is a second order effect compared to the response due to bending, it has not yet been determined that this is true for all types of flaps with strain gauges since the experience of the present invention has only been with one type of flap—that of a polyimide flap. Flaps that contain strengthening elements along the length of the flap should demonstrate less creep effect.

FIGS. 21(a) and 21(b) show a typical polymer creep stress-strain response plot that characterizes polymer creep. FIG. 21(a) is a graph of the stress σ(t) applied to the flap over time and FIG. 21(b) provides the physical strain of the flap, ε(t), under that stress function. The relationship of the response is described generally by the first order differential equation provided FIG. 21(c), a solution for which is provided as a convolution integral in FIG. 21(d). As shown in the flap response profile at FIG. 21(b), when the motion of the strain gauge is stopped, a relaxation is observed that is consistent with a polymer creep model. Numerous models may be used to approximate the functioning of the polymer creep such a Hookean spring and a Newtonian dashpot connected in parallel for use with viscoelastic materials (Kelvin-Voigt model). Regardless of the appropriate model, however, the error corrections achieved to date are through the empirical-based methods described below.

Since creep is introduced during both halves of the input cycling, e.g. whether the flap is being impinged with a positive or a negative air impulse, there will be a stretching of the flap during a low frequency, repetitive cycling sequence such that the response function of the flap has a positive baseline drift, i.e. an error that causes the flap to provide an imperfect response vis-à-vis the voltage baseline response of the sensor as obtained when the sensor has no input. Ideally, the Kapton® a correction function should be applied to the sensor output of the present invention to account and correct for this. For the mass-produced, off-the-shelf sensors, it is expected that the impact of elastic polymer creep on strain gauge output depends on the distance from base to strain gauge at which the Kapton® flap is fixed in the device and on the fraction of orifice area blocked by the flap, which will determine the stretching force on the flap and thus the amount of elastic polymer creep. With mass-produced sensors, these parameters should be constant from sensor-to-sensor and can be accommodated by mathematical correction in the software of the present invention.

Figure 22:
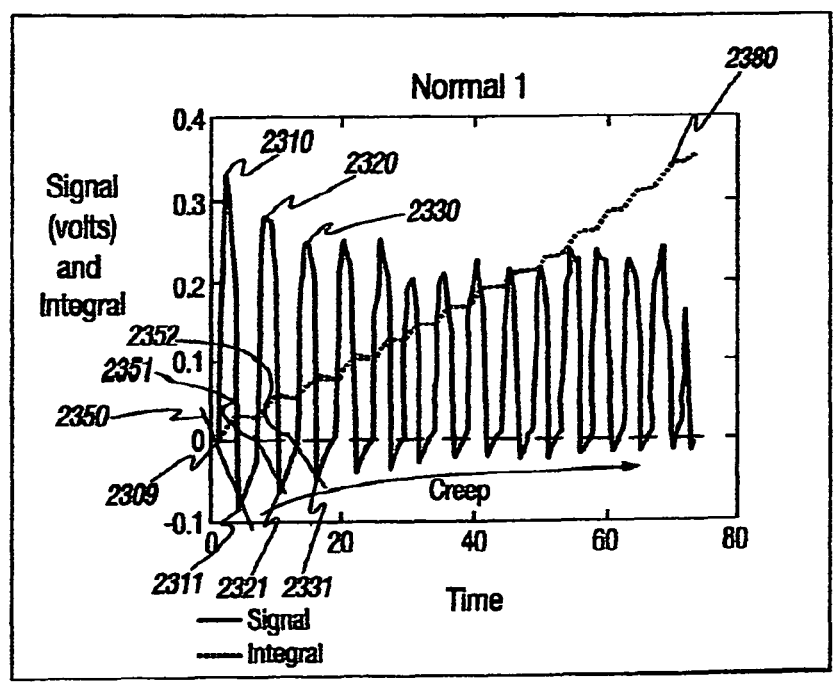
FIG. 22 provides a sensor response function in response to a testing method preformed according to one aspect of the present invention.
Figure 23:
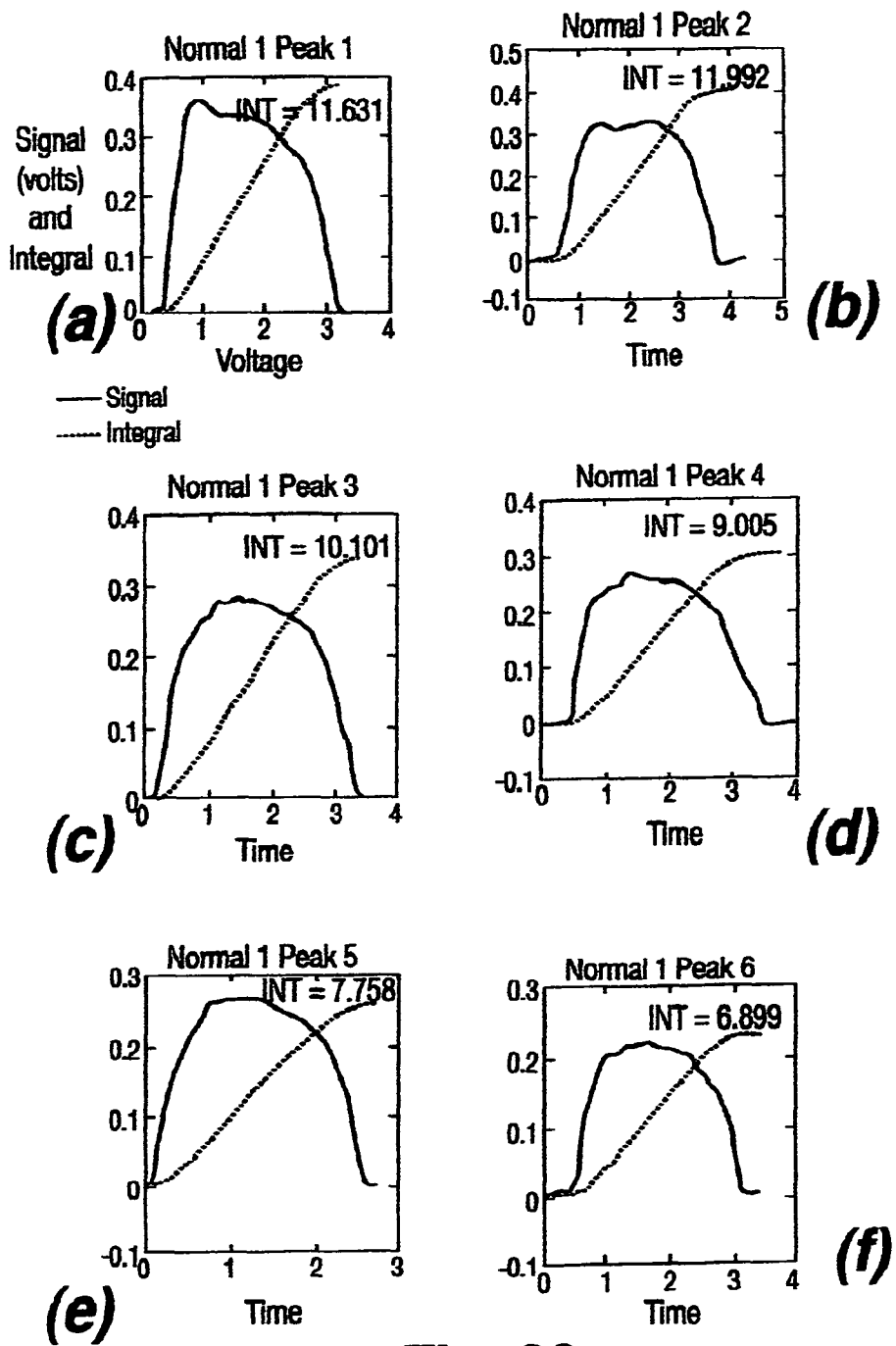
FIGS. 23($a$) through 23($f$) provide peak-by-peak corrected response functions of FIG. 22 according one method of polymer creep elimination of the present invention.

FIG. 22 shows a sensor response resulting from a series of positive air pulses of equal volume. It can be seen from the response that the first peak occurs at 2310 and then when the input has halted, the response function dips below the zero line to stop at the most negative point 2311. This continues from peak-to-peak on the positive side of the pulses with some degradation of the peak highs, 2320, 2330 etc., as the sequence of pulses is repeated. Also, the negative depth of the lower peaks 2311, 2321, 2331 etc. progressively gets smaller and asymptotically approaches the zero line as steady-state operation is achieve. There are two problems with the response as shown in FIG. 22. First, the negative peaks extending below the zero line do not accurately represent the actual air flow through the meter. There have been no negative pulses introduced as inputs. Therefore integration of the signal voltage (as converted to flow rates with the assistance of the calibration charts) over the pulse time will not provide an accurate incident volume. Second, the "moving up" of the most negative point of the pulses is evidence of polymer creep in the flap (shown by the curved line in the figure). Although this creep damps out once steady state is reached, a correction function needs to be applied upon initial response to remove the creep and more accurately represent the voltage waveform.

Similar to the use of the derivative function as with FIG. 20 above, a running first derivative function can be run on the sensor data points as accumulated (steps 2510 and 2520 FIG. 24) to identify the beginning of the first pulse at 2309 and the end of that pulse at 2311 (step 2530 FIG. 24). Similarly the beginning and end of the remaining pulses may be identified. To correct for the polymer creep, an error function consisting of the straight line functions represented by 2350, 2351 and 2352 may be calculated (step 2540 FIG. 24) by approximating a straight line function between the above-determined beginning and end points of the pulse. Knowing that the pulse cannot be negative, the error function may be added back into (in actuality a negative number subtracted from—step 2550 FIG. 24) the first peak to create normalized peaks that have baselines normalized to zero ("straightening" the baseline). FIGS. 23(a)-23(f) show the resulting peaks for the first 6 peaks when this normalization is performed. It can be seen that the positive pulse shapes are restored somewhat and more accurately represent the constant volume input pulse. These pulses may now be integrated to calculate sensor voltages (flow volumes after calibration curves are employed) as shown by the blue lines on each of the FIGS. 23(a)-23(g) (steps 2560 and 2570 of FIG. 24). The blue line on FIG. 22 shows the summed error signal due to the polymer creep and the resulting baseline shift. This curve flattens out as the system reached steady state operation over time.

FIG. 24 shows two basic flow diagrams providing exemplary steps for determining first and second order correction functions according to a preferred embodiment of the present invention. FIG. 24(a) provides the steps associated with a first order correction function as described substantially above with respect to FIGS. 22 and 23. FIG. 24(b) provides the steps associated with a second and higher order correction functions that may be employed by the flow meter and sensors of the present invention as described below.

Figure 25:
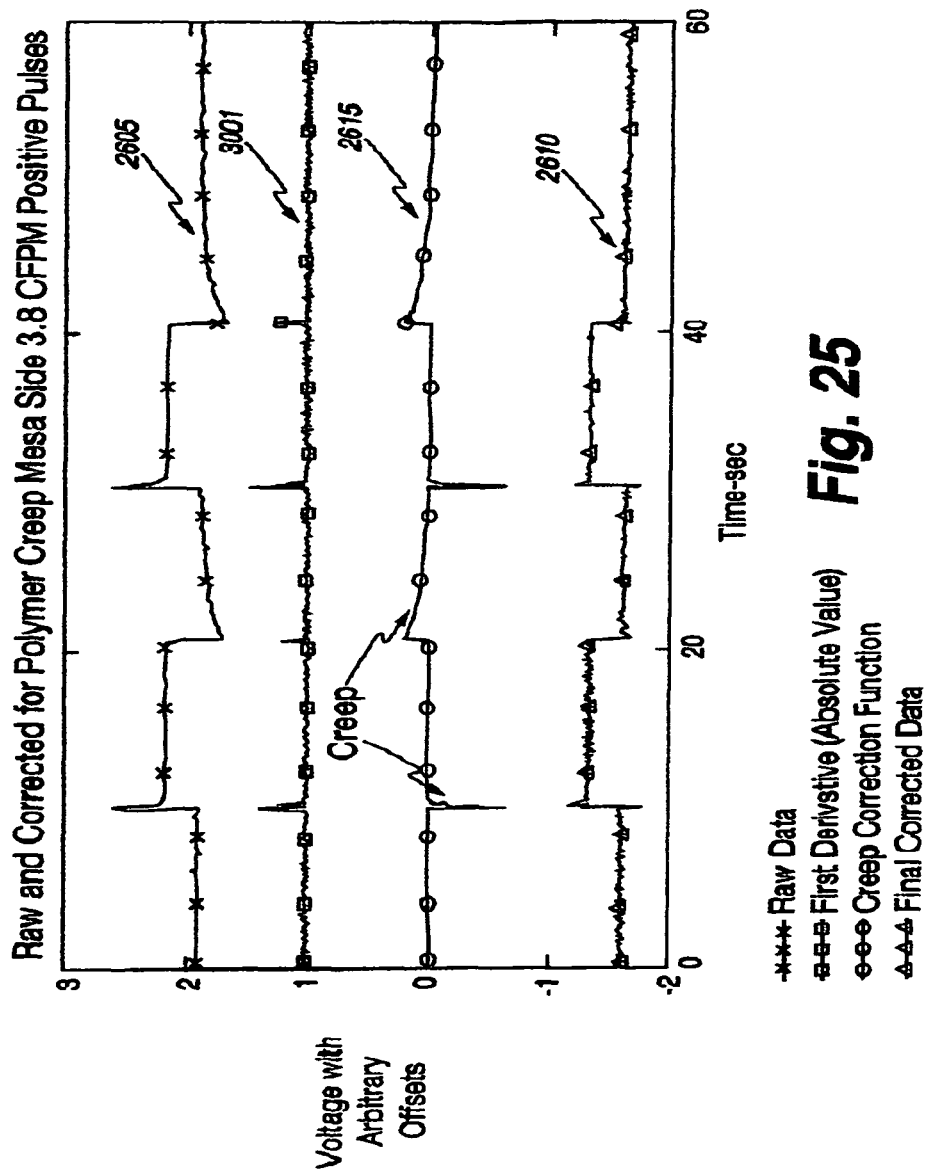
FIG. 25 provides additional graphs related to polymer creep and correction of the same according to another aspect of the present invention.

FIG. 25 shows another way to correct second order creep correction functions. This waveform shaping is similar to the exponential decay correction described above except that the correction function is the creep itself and not some other deterministic function. Shown in FIG. 25 is the raw sensor data 2605 from two cycles of a mesa side positive fluid impulse as recorded by the sensor and the flap within the flow meter at 3.8 CFPM. The first derivative curve 3001 of the raw data is also presented in FIG. 25 and is an indicator of when the creep functions starts in time. Polymer creep is shown and indicated with arrows on 2615. When the first air pulse is applied there is observed a sharp delta function like response. After the pulse, the flap relaxes due to the removal of stress with a slower time constant, again due to polymer creep.

Instead of simply squaring off the plateau or applying other correction functions, a second order polymer creep function 2615 may be calculated at step 2580 of FIG. 24 and subsequently subtracted from the raw data to arrive at a corrected data waveform 2610. The total corrective creep function consists of two exponential functions of the type:

$$\text{correction} = \frac{a - e^{-\frac{time}{b}}}{c}$$

with the constants, a, b, c being experimentally determined. It should be noted that this same procedure would work on the exponential side of positive input functions although the polymer creep function would be a bit more sever and subsequent correction may be less accurate.

Figure 26:
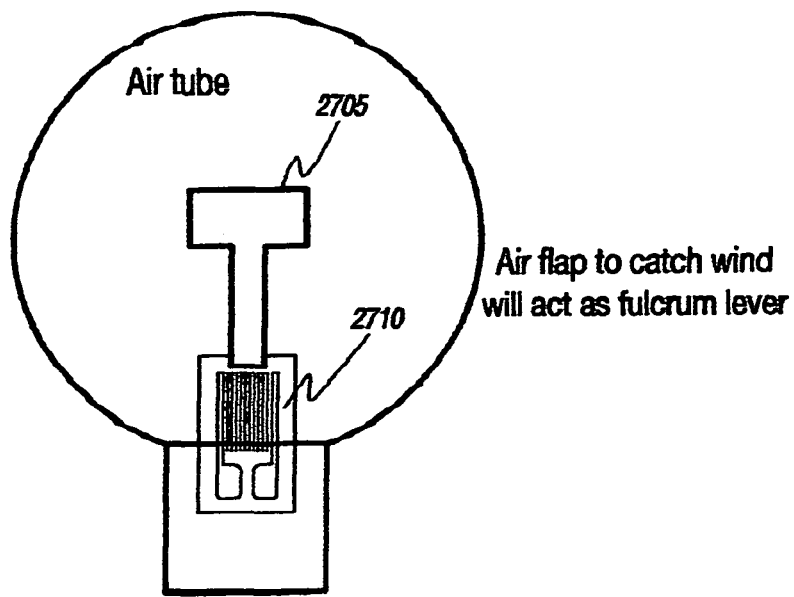
FIG. 26 is a flap for measuring airflow according to one preferred embodiment of the invention.

FIG. 26 shows a flap 2705 and sensor 2710 combination that provides little resistance to air flow and has the capability to magnify signals due to a fulcrum lever effect. Ideally, the flap 2705 will be a thin flexible plastic like Kapton®. Both 3 Hz and 5 Hz signals easily detected by this flap. Further, the sensor a) shows quick response to changes in air velocity, b) is very responsive to low air velocities, c) shows a good mesa side and an exponential side that has a repeatable exponential decay, d) is low cost, has a simple form factor, and sterilizes easily.

The present invention provides a new class of airflow sensors, in which the indicator of airflow is the elastic deformation of a flexible flap. The flexible flap does not require additional appendages for controlling vibration. The elimination of additional appendages prevents trapping of respiratory secretions and results in a device that is easy to clean and disinfect. The primary intended use of the airflow sensor according to the present invention is medical measurement of human respiratory airflow and breathing sounds for diagnostic and therapeutic purposes. However, the primary intended use should not be construed as limiting. Multiple embodiments are envisioned in which the flap can accommodate a plurality of other physical and chemical sensors.

The present invention is not limited to medical applications. An exemplary non-medical use of the present invention may be the measurement of airflow across the various surfaces of aircraft in flight. The airflow sensors of the present invention may be used to measure airflow with the particular advantage that the elastic flap devices of the present invention are very sensitive under stall conditions. Unlike pilot tubes, flaps built into the wings and bodies of commercial jet aircraft do not plug up with ice.

Another exemplary non-medical implementation of the present invention is a device mounted at the top of a mast of a sailboat that measures the wind speed, direction, and sound. The device may have a strain gauge in a tube. As wind goes through the tube, the sensor is bent, giving a change in resistance. The gauge may be connected to a cable capable of 360 degree rotation. A Wheatstone bridge may be used to monitor the change in resistance. The measurements of the strain gauge may be conveyed to a computing device. Using the sound card of the computing device, the user may hear low frequency sound indicative of adverse sail flapping, which could tell the user that a stall condition has occurred.

Other potential non-medical applications include monitoring air flow and vibrations in acoustical wind instruments from pipe organs to saxophones. Both medical and industrial embodiments of the airflow sensor can be modular, allowing cleaning and disinfection of the sensor.

While the invention has been shown and described with reference to specific preferred embodiments, it should be understood by those skilled in the art that various changes in form and detail may be made therein without departing from the spirit and scope of the invention as defined by the following claims.

What is claimed is:
1. A fluid flow sensing system comprising:
   a housing having a chamber that is sized and dimensioned to allow fluid to pass therethrough;
   a flap provided within said chamber, wherein the fluid causes said flap to move when the fluid passes thereover;
   a sensor coupled to said flap for generating an output signal when said flap moves, said sensor configured to sense a displacement of said movable flap in at least two directions;
   a determining unit for receiving said output signal of said sensor and in response thereto, determining flow rate data associated with the fluid;
   a correction unit for receiving said flow rate data and applying a correction function to said flow rate data to correct for a non-linear response of said flap; and wherein said non-linear response is an exponential decay of said flap response and said correction function corrects said exponential decay.

2. The system of claim 1 wherein said correction function is a straight-line approximation.

3. The system of claim 1 wherein said correction function is an exponential function based upon said exponential decay.

4. A fluid flow sensing system comprising:
a housing having a chamber that is sized and dimensioned to allow fluid to pass therethrough;
a flap provided within said chamber, wherein the fluid causes said flap to move when the fluid passes thereover;
a sensor coupled to said flap for generating an output signal when said flap moves, said sensor configured to sense a displacement of said movable flap in at least two directions;
a determining unit for receiving said output signal of said sensor and in response thereto, determining flow rate data associated with the fluid;
a correction unit for receiving said flow rate data and applying a correction function to said flow rate data to correct for a non-linear response of said flap; and
wherein said non-linear response is a baseline drift of said flap response and said correction function corrects for said baseline drift.

5. The system of claim 4 wherein said baseline drift is integrated over time to create said correction function.

6. A fluid flow sensing system comprising:
a housing having a chamber that is sized and dimensioned to allow fluid to pass therethrough;
a flap provided within said chamber, wherein the fluid causes said flap to move when the fluid passes thereover;
a sensor coupled to said flap for generating an output signal when said flap moves, said sensor configured to sense a displacement of said movable flap in at least two directions;
a determining unit for receiving said output signal of said sensor and in response thereto, determining flow rate data associated with the fluid;
a correction unit for receiving said flow rate data and applying a correction function to said flow rate data to correct for a non-linear response of said flap; and
wherein said correction function is empirically determined.

7. A fluid flow sensing system comprising:
a housing having a chamber that is sized and dimensioned to allow fluid to pass therethrough;
a flap provided within said chamber, wherein the fluid causes said flap to move when the fluid passes thereover;
a sensor coupled to said flap for generating an output signal when said flap moves, said sensor configured to sense a displacement of said movable flap in at least two directions;
a determining unit for receiving said output signal of said sensor and in response thereto, determining flow rate data associated with the fluid;
a correction unit for receiving said flow rate data and applying a correction function to said flow rate data to correct for a non-linear response of said flap; and
wherein said sensor is a piezoresistive sensor and said determining unit further comprises:

a voltage conversion unit for receiving said output signal of said sensor and converting said output signal into a voltage output signal;
an amplification unit for receiving said voltage output signal and generating an amplified voltage output signal;
a converter for converting said amplified voltage output signal into a digital output signal; and
a calculation unit for determining said air flow rate of the air based upon the digital output signal.

8. A fluid flow sensing system comprising:
a housing having a chamber that is sized and dimensioned to allow fluid to pass therethrough;
a flap provided within said chamber, wherein the fluid causes said flap to move when the fluid passes thereover;
a sensor coupled to said flap for generating an output signal when said flap moves, said sensor configured to sense a displacement of said movable flap in at least two directions;
a determining unit for receiving said output signal of said sensor and in response thereto, determining flow rate data associated with the fluid;
a correction unit for receiving said flow rate data and applying a correction function to said flow rate data to correct for a non-linear response of said flap; and
wherein said determining and correction units are provided as software modules within a general-purpose computer, said general purpose computer coupled to said sensor and including a processor and a memory.

9. A method for determining a flow rate of a fluid using a sensor coupled to a flap, said sensor generating an output signal when said flap moves, said method comprising:
providing a flow of said fluid across said sensor;
sensing a displacement of said flap with said sensor, said displacement being representative of a flow rate associated with said fluid flow;
generating said output signal from said sensor;
determining from said output signal said flow rate of said fluid flow from said sensed displacements;
correcting said flow rate data by applying a correction function to correct a non-linear response of said flap; and
wherein said non-linear response is an exponential decay of said flap response and said correcting step includes approximating said correction with a straight line.

10. A method for determining a flow rate of a fluid using a sensor coupled to a flap, said sensor generating an output signal when said flap moves, said method comprising:
providing a flow of said fluid across said sensor;
sensing a displacement of said flap with said sensor, said displacement being representative of a flow rate associated with said fluid flow;
generating said output signal from said sensor;
determining from said output signal said flow rate of said fluid flow from said sensed displacements;
correcting said flow rate data by applying a correction function to correct a non-linear response of said flap; and
wherein said non-linear response is an exponential decay of said flap response and said correcting step includes applying an exponential decay correction function.

11. A method for determining a flow rate of a fluid using a sensor coupled to a flap, said sensor generating an output signal when said flap moves, said method comprising:
providing a flow of said fluid across said sensor;

sensing a displacement of said flap with said sensor, said displacement being representative of a flow rate associated with said fluid flow;

generating said output signal from said sensor;

determining from said output signal said flow rate of said fluid flow from said sensed displacements;

correcting said flow rate data by applying a correction function to correct a non-linear response of said flap; and wherein said non-linear response is a baseline drift of said flap response and said correcting step includes applying a baseline drift correction function.

12. The method of claim 11 wherein said step of applying said baseline drift correction function includes integrating portions of said flow rate data.

13. A non-transitory, machine-readable, storage media having executable instructions for causing a processor within a computer-based system to perform a method for determining a flow rate of a fluid using a sensor coupled to a flap, said sensor generating an output signal when said flap moves, said machine-readable, storage media having steps for performing the method of:

providing a flow of said fluid across said sensor;

sensing a displacement of said flap with said sensor, said displacement being representative of a flow rate associated with said fluid flow;

generating said output signal from said sensor;

determining from said output signal said flow rate of said fluid flow from said sensed displacements;

correcting said flow rate data by applying a correction function to correct a non-linear response of said flap; and wherein said non-linear response is an exponential decay of said flap response and said correcting step includes applying an exponential decay correction function.

* * * * *